US012297328B2

(12) United States Patent
Quirk et al.

(10) Patent No.: US 12,297,328 B2
(45) Date of Patent: May 13, 2025

(54) DEPOLYMERIZATION OF A POLYHYDROXYALKANOATE AND RECYCLING OF HYDROXYALKONOATE MONOMER OBTAINED THEREBY VIA A METABOLIC PROCESS

(71) Applicant: Kimberly-Clark Worldwide, Inc., Neenah, WI (US)

(72) Inventors: Stephen Quirk, Alpharetta, GA (US); Peter B. Dulcamara, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 18/686,912

(22) PCT Filed: Sep. 30, 2021

(86) PCT No.: PCT/US2021/052826
§ 371 (c)(1),
(2) Date: Feb. 27, 2024

(87) PCT Pub. No.: WO2023/055373
PCT Pub. Date: Apr. 6, 2023

(65) Prior Publication Data
US 2024/0352215 A1 Oct. 24, 2024

(51) Int. Cl.
*C08J 11/10* (2006.01)
*C12N 1/20* (2006.01)
*C12P 7/625* (2022.01)
*C12R 1/385* (2006.01)
*C12R 1/63* (2006.01)
*C12R 1/64* (2006.01)

(52) U.S. Cl.
CPC ............ *C08J 11/105* (2013.01); *C12N 1/20* (2013.01); *C12P 7/625* (2013.01); *C08J 2367/04* (2013.01); *C12R 2001/385* (2021.05); *C12R 2001/63* (2021.05); *C12R 2001/64* (2021.05)

(58) Field of Classification Search
None
See application file for complete search history.

(56) References Cited

U.S. PATENT DOCUMENTS

| | | | |
|---|---|---|---|
| 8,129,590 B2 * | 3/2012 | Maranta | C12N 9/18 800/278 |
| 9,476,073 B2 | 10/2016 | Boisart | |
| 10,124,512 B2 | 11/2018 | Boisart et al. | |
| 10,508,269 B2 | 12/2019 | Li et al. | |
| 10,597,506 B2 | 3/2020 | Ibrahim et al. | |
| 10,767,026 B2 | 9/2020 | Desrousseaux et al. | |
| 2006/0280721 A1 * | 12/2006 | Veech | C07H 13/04 424/78.37 |
| 2009/0151026 A1 * | 6/2009 | Maranta | C12N 15/8257 435/320.1 |
| 2018/0230286 A1 | 8/2018 | Stubblefield et al. | |

FOREIGN PATENT DOCUMENTS

| | | |
|---|---|---|
| KR | 101273599 B1 | 6/2013 |
| WO | WO2015097104 A1 | 7/2015 |

OTHER PUBLICATIONS

Arias et al., Tight coupling of polymerization and depolymerization of polyhydroxyalkanoates ensures efficient management of carbon resources in Pseudomonas putida, Microbial Biotechnology, vol. 6, No. 5, 2013, pp. 551-563, https://doi.org/10.1111/1751-7915.12040.
Ballerstedt et al., MIXed plastics biodegradation and UPcycling using microbial communities: EU Horizon 2020 project MIX-UP started Jan. 2020, Environmental Sciences Europe, 2021, 9 pages.
PCT Search Report Corresponding to Application No. PCT/US2021/052826 on Jan. 31, 2022.
Doi et al., Cyclic nature of poly(3-hydroxyalkanoate) metabolism in Alcaligenes eutrophus, FEMS Microbiology Letter, vol. 67, No. 1-2, 1990, pp. 165-169, https_//doi.org/10.1111/j.1574-6968.1990.tb13856.x.
Gasser et al., Ecology and characterization of polyhydroxy alkanoate-producing microorganisms on and in plants, FEMS Microbiology Ecology, vol. 70, No. 1, 2009, pp. 142-150, https://doi.org/10.1111/j.1574-6941.2009.00734.x.
Gholami et al., Bacterial Strain Isolated from High-Salt Environments Can Produce Large Amounts of New Polyhydroxyalkanoate (PHA), Journal of Environmental Treatment Techniques, vol. 8, Issue 4, 2020, pp. 1268-1273, https://doi.org/10.47277/JETT/8(4)1273.
Kobayashi et al., Disruption of poly (3-hydroxyalkanoate) depolymerase gene and overexpression of three poly (3-hydroxybutyrate) biosynthetic genes improve poly (3-hydroxybutyrate) production from nitrogen rich medium by Rhodobacter sphaeroides, Microbial Cell Factories, vol. 18, No. 1, 2019, pp. 1-13, https://doi.org/10.1186/s12934-019-1088-y.

(Continued)

*Primary Examiner* — Blaine Lankford
(74) *Attorney, Agent, or Firm* — Dority & Manning, P.A.

(57) ABSTRACT

A process is disclosed for production of a polyhydroxyalkanoate that includes depolymerization of a post-consumer polyhydroxyalkanoate and utilization of the hydroxyalkanoate monomer thus produced as a carbon source for a microorganism capable of production of a polyhydroxyalkanoate. Methods can be utilized for true cyclic use of polyhydroxyalkanoates including polyhydroxybutyrates. Various aspects are described including simultaneous depolymerization and polymer production, utilization of purified depolymerase enzymes and/or microorganisms that express a depolymerase in conjunction with a microorganism that produces polymer, utilization of microorganisms that produce both a depolymerase and a new polymer, and utilization of genetically modified organisms to produce natural or modified depolymerase enzymes.

18 Claims, 10 Drawing Sheets

(56) References Cited

OTHER PUBLICATIONS

Myung et al., Disassembly and reassembly of polyhydroxyalkanoates: Recycling through abiotic depolymerization and biotic Repolymerization, Biosource Technology, vol. 170, 2014, pp. 167-174, https://doi.org/10.1016/j.biortech.2014.07.105.

Nikolaivits et al., Progressing Plastics Circularity: A Review of Mechano-Biocatalytic Approaches for Waste Plastic (Re)valorization, Frontiers in Bioengineering and Biotechnology, vol. 9, 2021, 31 pages, https://doi.org/10.3389/fbioe.2021.696040.

Sato et al., Utilization of 2-alkenoic acids for biosynthesis of medium-chain-length polyhydroxyalkanoates in metabolically engineered *Escherichia coli* to construct a novel chemical recycling system, Polymer Degradation and Stability, vol. 97, Issue 3, 2012, pp. 329-336, https://doi.org/10.1016/j.polymdegradstab.2011.12.007.

Tokiwa et al., Biotechnological production of (R)-3-hydroxybutyric acid monomer, Journal of Biotechnology, vol. 132, Issue 3, 2007, pp. 264-272, ttps://doi.org/10.1016/j.jbiotec.2007.03.015.

\* cited by examiner

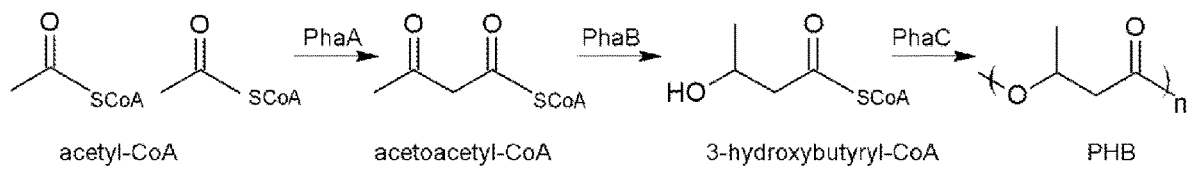

FIG. 1
Prior Art

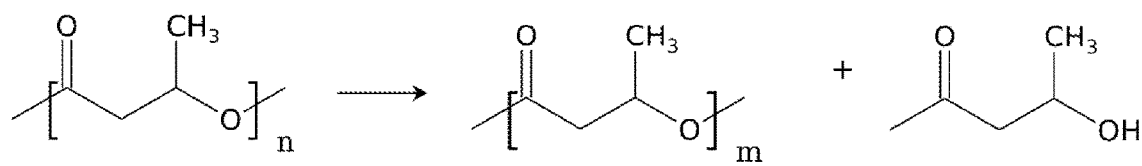

FIG. 2
Prior Art

```
         10          20          30          40          50          60
GSSEVAGFGS  NPGNLRMFAY  VPPNLPADAP  LVVALHGCSQ  SAASYDNETG  WEMLAQRWRF 70          80          90         100         110         120
AVLLPQQQSA  NNSSACFNWF  ETADTTRGQG  EALSVKQMID  RMRADHAVSA  SRVYVTGLSA 130         140         150         160         170         180
GGAMAAALLA  TYPDVFAGGA  IVAGIPYRCA  TSSSAAFSCM  SPGSDLTPQQ  WGDKVRAASA 190         200         210         220         230         240
HTGPWPIVSL  WQGDADYLVR  PINQSELMQQ  WTNVHGIDQT  PDVQDNLAGV  PHKVYRDAAG 250         260         270         280         290         300
RARVETYTVA  GMGHGVPVDP  GSGETQCGAA  GAYILDVNIC  SSYYIARFWG  LDDLDPNPPQ 310         320         330         340         350         360
VALTAPADGA  QVSGTVTLAA  QASDDVGVER  VEFLLDGALL  GSDASAPYSL  PWNSANAGNG 370         380         390         400         410         420
AHTLQARAFD  LAGNSASSAA  IAVQVSGGGS  APLTMEFDNE  DGNDGYVKAN  ADGSAAAIGT 430         440         450         460         470         480
LEATYGLASG  RGADGKHNRS  VLSFDTSALP  DGAQILAATL  SVGFGSAYGD  PWSQPAGNRL 490         500         510         520         530         540
LIDARRGCFG  GCAIEAGDYA  AAADASAVAE  LARFSGGRQT  SSAFDAAGLA  AIDRTGRTQL 550         560         570
RLRFEQPPAA  TNYLWIERGA  SAKLRVEYRP
```

FIG. 3

DEPOLYMERIZATION OF A POLYHYDROXYALKANOATE AND RECYCLING OF HYDROXYALKONOATE MONOMER OBTAINED THEREBY VIA A METABOLIC PROCESS

RELATED APPLICATIONS

The present application is the national stage entry of International Patent Application No. PCT/US2021/052826 having a filing date of Sep. 30, 2021, which is incorporated herein in its entirety by reference thereto.

BACKGROUND

It has been estimated that over 300,000,000 metric tons of petroleum-based polymers are being produced each year with global production continuing to increase. A significant portion of these polymers are used to produce single-use products, such as plastic drinking bottles, straws, packaging, and personal care products. Most of these plastic products are discarded and do not enter the recycle stream. As the worldwide single-use plastic epidemic worsens, it becomes paramount to identify fully renewable plastics and develop methods and materials that provide for industrial processing of renewable plastics.

Biodegradable polymers produced from renewable resources (also termed "biopolymers") hold great promise for reducing the global accumulation of petroleum-based plastics in the environment. One such class of biopolymers are the polyhydroxyalkanoates (PHA). Much work has been accomplished on the PHA family, most notably the polyhydroxybutyrate (PHB) polymers including poly-3-hydroxybutyrate (P3HB), poly-4-hydroxybutyrate (P4HB), polyhydroxyvalerate (PHV), polyhydroxyhexanoate (PHH), polyhydroxyoctanoate (PHO) and their copolymers. Of particular advantage, PHA exhibit thermoplastic properties that are very similar to some petroleum-based polymers and thus represent viable replacements for petroleum-based polymers such as polypropylene and polyethylene.

PHA are naturally produced across many bacterial, fungal, and archaeal lineages including *Azotobacter, Ralstonia, Burkholderia, Protomonas, Bacillus*, and *Schlegelella* for use as an energy sink. Production of PHA polymers involves a three-step enzymatic mechanism that begins with acetyl coenzyme A (acetyl-CoA). As indicated in FIG. 1, the first step is catalysis of acetyl-CoA by PhaA (a β-ketothiolase) to form acetoacetyl-CoA. This in turn is converted in a NADP-dependent reaction into R-3-hydroxybutyrryl-CoA by the PhaB enzyme (a β-ketoacyl-CoA reductase). The final step is catalyzed by PhaC (a PHB synthase), and is the polymerization of the monomer to form PHA, e.g., PHB as indicated in FIG. 1. Bio-synthesized polyhydroxyalkanoates accumulate in the bacterial cell as large molecular weight granules and can account for from about 60% to about 90% of the cellular dry mass In nature, to retrieve the energy stored in the polymer, biodegradation is accomplished by a PHA depolymerase (PHADase) that is expressed by the organism and that degrades the polymer back to hydroxyalkanoate (HA) monomer and small PHA oligomers as indicated in FIG. 2 for PHB degradation to form HB monomer. In nature, the monomer is then further degraded to provide a carbon and energy source for the organism. Unfortunately, while the monomer can be fully environmentally degraded, it is a dead-end from an industrial standpoint as it cannot be directly repolymerized by any known chemical process.

Even though biopolymers are capable of biodegrading significantly faster than petroleum-based polymers, biopolymers still remain in landfills or the soil for significant periods of time once discarded. Thus, a need exists for systems and processes that can fully recycle biopolymers. A truly circular use of a bioplastic that is capable of breaking down the polymer into the monomer units and then utilize that monomer as a carbon source to create new polymer would make significant advances in waste disposal processes. It would be a further benefit if the recycled and reformed biopolymer is suitable for use in consumer products and industrial processes. Specifically, it would be economically and environmentally advantageous to utilize post-consumer HA monomer obtained according to a post-consumer recycling process as a carbon source for microorganisms capable of producing PHA suitable for reuse in formation of new product. A process and system that incorporates both the depolymerization and metabolic polymer formation aspects would be particularly beneficial and provide a truly cyclic biopolymer utilization approach.

SUMMARY

In general, the present disclosure is directed to methods and systems for degradation of PHA polymers and production of new PHA polymers by metabolic use of the degradation products. The PHA polymers fed to a process can be components of post-consumer materials, such as post-consumer personal care products, food industry products, packaging, post-consumer medical products, post-consumer industrial products, and other articles containing recyclable PHA. The present disclosure is directed to a truly cyclic process that can be used for single system biodegradation combined with formation of new biopolymers in small or large settings.

A process can include contacting a post-consumer product that includes a PHA with a PHADase. Upon the contact, HA monomer can be released from the PHA. A process also includes providing the post-consumer HA monomer thus obtained as a carbon source to a microorganism capable of metabolizing the HA. The microorganism is one that can produce PHA and the HA monomer can be provided to the microorganism at growth conditions configured to encourage metabolic PHA production by the microorganism. For instance, the HA monomer can be provided to the microorganism under metabolic stressful conditions, e.g., with HA as the only available carbon source or with any other carbon source at low concentration and/or at low or no presence of other nutrients such as nitrogen and/or phosphorous.

In one aspect, the PHA and HA can be PHB and HB. In one aspect, one or both of the depolymerization component and the microorganism monomer metabolism component can be carried out at an extreme condition such as extreme temperature, pressure, salt content, etc., or combinations thereof. In such an embodiment, a procedure can decontaminate the feedstock as well as providing new biopolymer. In addition, the two components of a process can be carried out at the same conditions as one another or at conditions that differ in some aspect from one another (e.g., temperature, pressure, salt content, etc.). The depolymerization of a post-consumer polymer and the utilization of the produced monomer as a carbon source for microorganism metabolism can be carried out simultaneously to one another (e.g., in parallel bioreactors), immediately sequentially to one another (e.g., direct feed between bioreactors in series) or at different times and/or locations to one another. In some embodiments, these two components of a process can be carried out together in a single bioreactor.

Depolymerization of a post-consumer product to obtain a post-consumer HA monomer can be carried out according to an enzymatic process that utilizes one or more natural PHADase, one or more modified PHADase, or combinations thereof. For instance, a post-consumer product can be contacted with a purified enzyme to provide HA monomer and the purified enzyme can be a naturally expressed enzyme or a modified purified enzyme that includes one or more modifications as compared to a naturally expressed enzyme. In some aspects, a post-consumer product can be contacted with a microorganism that produces an enzyme, and the microorganism can be one that naturally produces the enzyme, a microorganism that has been transformed to produce the enzyme, or a combination thereof. A microorganism transformed to produce a modified enzyme used in a process can be a microorganism that naturally produces a PHADase (the unmodified PHADase or a different PHADase) or a microorganism that does not naturally produce a PHADase.

In some aspects, a process can incorporate an enzymatic depolymerization component that can utilize a PHADase produced by a microorganism (or a modified version thereof), and the same microorganism can utilize the HA monomer thus produced as a carbon source in metabolic polymer production. The PHADase of such a process can include solely enzyme produced by (or derived from) the HA metabolizing microorganism. For instance, a process can include providing a post-consumer feed to a single microorganism that is capable of both expressing a PHADase for depolymerizing PHA of a feed and subsequently metabolizing the released HA to produce new PHA under the process conditions of a single bioreactor system. In some embodiments, the PHADase of such a process can include enzyme produced by (or derived from) the HA metabolizing microorganism in addition to additional PHADase produced by (or derived from) one or more additional microorganisms. As utilized herein, the term 'derived' with regard to an enzyme derived from a microorganism is intended to refer to a natural enzyme that has been purified following expression from a microorganism that naturally produces the enzyme, to a natural enzyme (either purified or not) that has been expressed from a microorganism that has been transformed to produce the enzyme, as well as to a modified enzyme (either purified or not) that includes one or more amino acid modifications as compared to a natural enzyme.

In some aspects, cocultures of microorganisms can be utilized that can include one or more microorganisms that can produce a PHADase for depolymerization of a post-consumer product in conjunction with one or more microorganisms that can utilize the monomer thus produced as a metabolic carbon source and that can produce a PHA under the culture conditions. Cocultures can utilize natural microorganisms, transformed microorganisms, or combinations thereof.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which:

FIG. 1 illustrates a natural metabolic reaction process for forming polyhydroxybutyrate (PHB) as is known in the art.

FIG. 2 illustrates a natural metabolic reaction process for degradation of PHB as is known in the art.

FIG. 3 provides the sequence (SEQ ID NO: 1) of a recombinant purified and cleaved *Lysobacter enzymogenes* PHBDase as may be utilized in disclosed methods.

Figure 4:
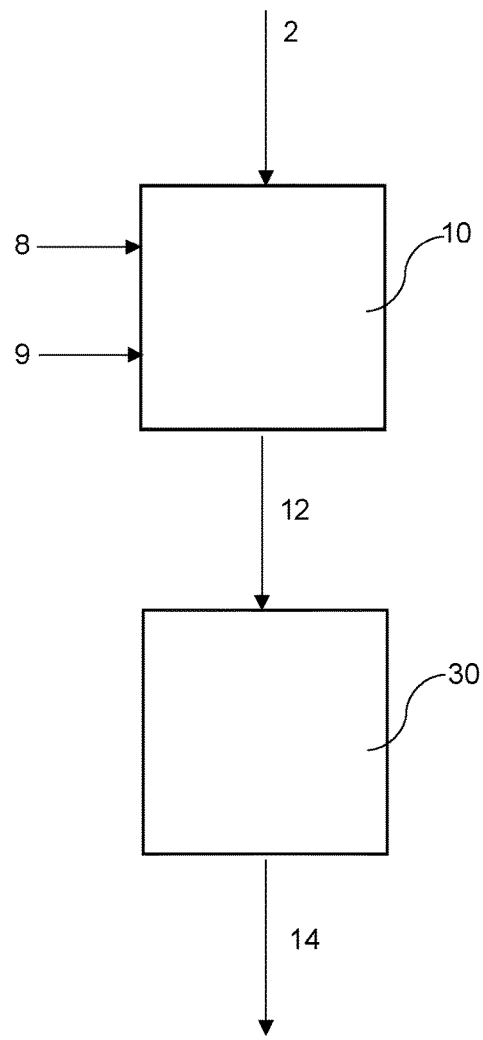
FIG. 4 schematically illustrates one embodiment of a bioreactor system as may be utilized in carrying out a process as disclosed herein.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

The present disclosure is directed to a truly circular use of a polyhydroxyalkanoate (PHA) that includes degradation/depolymerization of a PHA polymer to release hydroxyalkanoate (HA) monomer and utilization of the released monomer as a metabolic carbon source for a microorganism capable of production of new PHA polymer. Though by no means limited to such, in one embodiment, the method can be directed to treatment of post-consumer products that incorporate polyhydroxybutyrate (PHB).

The methods provide a route for recycling post-consumer PHA in conjunction with production of new industrially/commercially viable PHA. The methods incorporate an enzyme-based approach for depolymerization in conjunction with harnessing metabolic processes for utilization of the depolymerization product to produce new polymer. Thus, a fully recycled use of a biopolymer can be provided. The newly produced polymers are well suited to producing all different types of products including single-use products such as, without limitation, packaging, straws, cups, bottles, shopping bags, eating utensils, trays, and personal care products such as personal care garments (e.g., diapers, child training pants, disposable swim pants, feminine hygiene products, adult incontinence products), tampon dispensers, medical supplies, etc. Post-consumer products for use as a feed source in disclosed processes can be from any source (e.g., commercial, industrial, medical, etc.) and can include PHA in conjunction with other components, including other polymers and/or other non-polymeric materials, waste materials, labeling materials, etc. The use and re-use of biopolymers via a fully circular use of the polymer components to replace petroleum-based polymers will make significant strides in creating a sustainable economy.

Any product including a polymer that incorporates a recyclable PHA linear polyester as is produced in nature by bacterial fermentation of sugar or lipids can be processed according to the present disclosure. Likewise, PHA produced by disclosed methods can be utilized in forming any PHA-based polymer as is known in the art. As is known, more than 100 different monomers can be combined within this family to produce materials. Examples of monomer units that can be incorporated in a PHA as may be degraded and/or formed according to disclosed methods can include, without limitation, 2-hydroxybutyrate, glycolic acid, 3-hydroxybutyrate, 3-hydroxypropionate, 3-hydroxyvalerate, 3-hydroxyhexanoate, 3-hydroxyheptanoate, 3-hydroxyoctanoate, 3-hydroxynonanoate, 3-hydroxydecanoate, 3-hydroxydodecanoate, 4-hydroxybutyrate, 4-hydroxyvalerate, 5-hydroxyvalerate, and 6-hydroxyhexanoate.

A polymer can be a homopolymer or a copolymer. Examples of PHA homopolymers as can be processed and/or produced according to disclosed methods can include, without limitation, poly 3-hydroxyalkanoates (e.g., poly 3-hydroxypropionate (PHP), poly 3-hydroxybutyrate (PHB), poly 3-hydroxyvalerate (PHV), poly 3-hydroxyhexonoate (PHH), poly 3-hydroxyoctanoate (PHO), poly 3-hydroxydecanoate (PHD), and poly 3-hydroxy-5-phenylvalerate (PHPV)), poly 4-hydroxyalkanoates (e.g., poly 4-hydroxybutyrate (hereinafter referred to as PHB) and poly 4-hydroxyvalerate (hereinafter referred to as PHV)), or poly 5-hydroxyalkanoates (e.g., poly 5-hydroxyvalerate (hereinafter referred to as PHV)). One common type of PHA encompassed in the present disclosure is Poly (3-hydroxybutyrate) (PHB).

In certain aspects, a post-consumer product degraded according to disclosed methods and/or formed from PHA produced according to disclosed methods can include a PHA copolymer that can include solely PHA components or PHA components in combination with other types of polymer components. Examples of PHA copolymers include, without limitation, poly 3-hydroxybutyrate-co-3-hydroxypropionate (hereinafter referred to as PHB3HP), poly 3-hydroxybutyrate-co-4-hydroxybutyrate (hereinafter referred to as P3HB4HB), poly 3-hydroxybutyrate-co-4-hydroxyvalerate (hereinafter referred to as PHB4HV), poly 3-hydroxybutyrate-co-3-hydroxyvalerate (hereinafter referred to as PHB3HV), poly 3-hydroxybutyrate-co-3-hydroxyhexanoate (hereinafter referred to as PHB3HH) and poly 3-hydroxybutyrate-co-5-hydroxyvalerate (hereinafter referred to as PHB5HV).

Depolymerization

Irrespective of the particular PHA(s) included in a post-consumer product, a process can include enzymatic depolymerization of PHA of the post-consumer product. The present methods can utilize one or more depolymerase enzymes alone (e.g., purified PHADase), one or more microorganisms that can express one or more depolymerase enzymes, or combination of one or more PHADase expressing microorganisms with one or more added (purified) PHADase to break down PHA of a post-consumer product and provide HA monomer, which can then be utilized as a carbon source for a microorganism in production of newly formed polymer.

PHADase-expressing microorganisms can include those that naturally express the enzyme as well as those that have been modified to express the enzyme, which, likewise, can be an enzyme as found in nature or a modified enzyme. When utilizing one or more microorganisms that naturally express the discussed enzymes, or that have been modified to express the desired enzymes, the depolymerization component of a process may be referred to as a bacteria-based-enzymatic component of a process, rather than an enzyme-based component.

The PHADase or PAHDase-expressing microorganism utilized to degrade PHA of a post-consumer product is not particularly limited. In one embodiment, the enzyme that degrades a PHA can be a naturally occurring enzyme. For instance, in one aspect, the microorganism, or enzyme expressed therefrom, incorporated into a depolymerization component of a process can include a microorganism from a bacterial genera including, but not limited to, *Halomonas, Lihuaxuella, Lysobacter, Alteromonas, Arthrobacter, Azospirillum, Empedobacter, Desulfovibrio, Halobacillus, Halobacteriovorax, Haloechinothrix, Halomarina, Halorussus, Haloterrigena, Isoptericola, Marinobacter, Methyloligella, Micromonospora, Natronococcus, Nocardiopsis, Paracoccus, Roseivivax, Saccharomonospora, Shewanella, Alicyclobacillus, Natranaerobius, Halobacteriaceae, Hyphomonas, Amycolatopsis, Georgenia, Acidothermus,* and *Thermobifida,* as well as any combination thereof.

By way of example, one or more of the following organisms may be used in accordance with the present disclosure to provide enzymes of the present disclosure (whether as the microorganism itself or the purified enzyme): *Lysobacter aestuarii, Lysobacter antibioticus, Lysobacter bugurensis, Lysobacter capsica, Lysobacter enzymogenes, Lysobacter lacus, Lysobacter lycopersici, Lysobacter maris, Lysobacter niastensis, Lysobacter profundi, Lysobacter* sp., *Lysobacter* sp. A03, *Lysobacter* sp. cf310, *Lysobacter* sp. H21R20, *Lysobacter* sp. H21R4, *Lysobacter* sp. H23M41, *Lysobacter* sp. R19, *Lysobacter* sp. Root604, *Lysobacter* sp. Root690, *Lysobacter* sp. Root916, *Lysobacter* sp. Root983, *Lysobacter* sp. TY2-98, *Lysobacter spongiae, Lysobacter*

*spongiicola, Lysobacter, Lysobacter alkalisoli, Lysobacter arseniciresistens, Lysobacter daejeonensis, Lysobacter dokdonensis, Lysobacter enzymogenes, Lysobacter enzymogenes, Lysobacter gilvus, Lysobacter gummosus, Lysobacter maris, Lysobacter oculi, Lysobacter panacisoli, Lysobacter penaei, Lysobacter prati, Lysobacter psychrotolerans, Lysobacter pythonis, Lysobacter ruishenii, Lysobacter segetis, Lysobacter silvestris, Lysobacter silvisoli, Lysobacter soli, Lysobacter sp., Lysobacter sp. 17J7-1, Lysobacter sp. Alg18-2.2, Lysobacter sp. Cm-3-T8, Lysobacter sp. H23M47, Lysobacter sp. HDW10, Lysobacter sp. II4, Lysobacter sp. N42, Lysobacter sp. OAE881, Lysobacter sp. Root494, Lysobacter sp. URHA0019, Lysobacter sp. WF-2, Lysobacter sp. yr284, Lysobacter tabacisoli, Lysobacter telluris, Lysobacter tolerans, Lysobacter tolerans, Lysobacter xinjiangensis, unclassified Lysobacter, Aliivibrio finisterrensis, Aliivibrio fischeri, Aliivibrio sifiae, Aliivibrio sp., Aliivibrio sp. 1S128, Aliivibrio sp. EL58, Aliivibrio sp. SR45-2, Caballeronia arvi, Caballeronia calidae, Caballeronia hypogeia, Caballeronia insecticola, Caballeronia pedi, Caballeronia terrestris, Dokdonella koreensis, Dyella caseinilytica, Dyella choica, Dyella dinghuensis, Dyella flava, Dyella jiangningensis, Dyella kyungheensis, Dyella mobilis, Dyella monticola, Dyella nitratireducens, Dyella psychrodurans, Dyella soli, Dyella solisilvae, Dyella sp. 7MK23, Dyella sp. ASV21, Dyella sp. ASV24, Dyella sp. C11, Dyella sp. C9, Dyella sp. DHC06, Dyella sp. EPa41, Dyella sp. G9, Dyella sp. M7H15-1, Dyella sp. M7H15-1, Dyella sp. OK004, Dyella sp. S184, Dyella sp. SG562, Dyella sp. SG609, Dyella sp. YR388, Dyella tabacisoli, Fluoribacter bozemanae, Fluoribacter dumoffii NY 23, Fluoribacter gormanii, Microscilla marina, Pseudomonas aeruginosa, Pseudomonas thermotolerans, Pseudomonas mediterranea, Psychrobacter sp., Psychromonas sp. MB-3u-54, Psychromonas sp. psych-6C06, Psychromonas sp. RZ22, Psychromonas sp. Urea-02u-13, Rhodanobacter denitrificans, Rhodanobacter fulvus, Rhodanobacter glycinis, Rhodanobacter lindaniclasticus, Rhodanobacter panaciterrae, Rhodanobacter sp. 7MK24, Rhodanobacter sp. A1T4, Rhodanobacter sp. B04, Rhodanobacter sp. B05, Rhodanobacter sp. C01, Rhodanobacter sp. C03, Rhodanobacter sp. C05, Rhodanobacter sp. C06, Rhodanobacter sp. DHB23, Rhodanobacter sp. DHG33, Rhodanobacter sp. L36, Rhodanobacter sp. MP1X3, Rhodanobacter sp. OK091, Rhodanobacter sp. OR444, Rhodanobacter sp. PCA2, Rhodanobacter sp. Root480, Rhodanobacter sp. Root627, Rhodanobacter sp. Root627, Rhodanobacter sp. SCN 67-45, Rhodanobacter sp. SCN 68-63, Rhodanobacter sp. Soil772, Rhodanobacter sp. T12-5, Rhodanobacter sp. TND4EH1, Rhodanobacter sp. TND4FH1, Rhodanobacter spathiphylli, Rhodanobacter thiooxydans, Stenotrophomonas chelatiphaga, Stenotrophomonas maltophilia, Stenotrophomonas panacihumi, Stenotrophomonas pavanii, Stenotrophomonas rhizophila, Stenotrophomonas sp. DDT-1, Stenotrophomonas sp. RIT309, Stenotrophomonas sp. SKA14, Vibrio aestuarianus, Vibrio antiquaries, Vibrio aquaticus, Vibrio tasmaniensis, Xanthomonadales bacterium, Xanthomonas albilineans, Xanthomonas arboricola, Xanthomonas axonopodis, Xanthomonas bromi, Xanthomonas campestris, Xanthomonas cannabis, Xanthomonas citri, Xanthomonas euvesicatoria, Xanthomonas fragariae, Xanthomonas hortorum, Xanthomonas hyacinthi, Xanthomonas oryzae, Xanthomonas phaseoli, Xanthomonas pisi, Xanthomonas sacchari, Xanthomonas sp. Leaf131, Xanthomonas sp. NCPPB 1128, Xanthomonas translucens, Xanthomonas vasicola, Xanthomonas vesicatoria*, or a combination thereof. It should be understood that the following list is exemplary only.

In some embodiments, a method can utilize extremophilic depolymerase enzymes (also referred to as extremozymes) that can function at an extreme environmental condition. As used herein, and as will be discussed in greater detail below, extremophilic refers to a microorganism, or an enzyme obtained from an extremophilic microorganism, that can tolerate one or more hostile environments, such as high salt, high temperature, elevated pressure, acidic, basic, or the like.

Extremophilic microorganism-derived enzymes or the microorganisms themselves can be utilized at selected environmental conditions during a depolymerization component of a process to improve any aspect of the process, e.g., production kinetics, production efficiency, production purity, etc. In some embodiments, utilization of extremophilic enzymes can reduce/eliminate the presence of contaminants in the processed materials such as, e.g., post-consumer diapers, as the processing at this stage can be carried out at an extreme condition (elevated temperature, high salt concentration, elevated pressures, etc.) at which the contaminant can be degraded. Eliminating or reducing contaminants in the materials can reduce risk to process operators and reduce the risk of process equipment contamination as well as allow for subsequent processing to be carried out without additional sterilization procedures prior to further treatment of the downstream product (e.g., culturing, polymer recovery and purification, etc.). Thus, the present disclosure allows for an efficient pathway to simultaneously sterilize the post-consumer products as well as depolymerize a PHA of the materials and form new PHA biopolymer.

Contaminants as may be present in post-consumer products that can be rendered non-pathogenic by utilization of an extremozyme (or extremozyme-expressing microorganism) at selected environmental conditions can include mesophilic pathogens such as, without limitation, viruses, bacteria, fungi, and protozoans, disclosed methods. As utilized herein, the terms "mesophile" and "mesophilic" refer to organisms that naturally exist in environmental conditions at which humans generally co-exist with the organism, including near human body temperature (e.g., from about 20° C. to about 45°), a saline content in water of from about 5 to about 18 parts per thousand (also referred to as mesohaline), about one atmosphere pressure (e.g., from about 20 kPa to about 110 kPa), and near neutral pH (e.g. from about pH 5 to about pH 8.5, also referred to as neutrophiles or neutrophilic). Typical bacterial pathogens can include those commonly found in human stool such as, and without limitation to, those of a genus *Streptococcus, Bifidobacterum, Lactobacillus, Staphylococcus, Clostridium, Enterobacteriaceae*, or *Bacteroides.*

The microorganism or collection of microorganisms for use in can be selected not only in order to secrete a particular PHA depolymerase, but can also be used based upon the environmental conditions in which the post-consumer product exists (e.g., in a waste material depository) or which a bioreactor contains. For example, the post-consumer material can be contained in an environment or a bioreactor may be designed to function in an environment that may be defined by a particular temperature range, salinity amounts, amount of oxygen, etc., or combinations thereof. Such particular environmental variables can be matched to one or more microorganisms, such as bacteria and/or archaea, best suited for the particular environment. For example, microorganism may be selected based upon the salt or temperature tolerance of the microorganism selected, or by modifying a microorganism having the desired salt or temperature tolerance to express an appropriate depolymerase enzyme. For instance, when a microorganism has a specific salt tolerance, expression of an appropriate depolymerase enzyme, and thus, degradation of PHA can be further increased and/or slowed based upon the desired degradation rate. The microorganism, for instance, can be a microorganism that naturally produces the desired enzyme or can be a microorganism that has been genetically modified or cloned in order to express the desired depolymerase gene.

In one aspect, a microorganism and/or enzyme produced by the microorganism may be tolerant of a concentration of a salt of about 0.5 M or greater, such as about 1M or greater, such as about 2M or greater, such as about 2.5M or greater, such as about 3 M or greater, such as about 3.5 M or greater, such as about 4 M or greater, such as about 4.5 M or greater, such as about 5 M or greater, such as about 5.5 M or greater, such as about 6 M or greater, such as about 6.5 M or greater, such as about 7 M or greater, or any ranges or values therebetween.

In another aspect, a microorganism and/or enzyme produced by the microorganism may be tolerant to a temperature of about 40° C. or greater, such as about 50° C. or greater, such as about 60° C. or greater, such as about 70° C. or greater, such as about 80° C. or greater, such as about 90° C. or greater, such as about 100° C. or greater, such as about 110° C. or greater, such as about 120° C. or greater, such as about 130° C. or greater, such as about 150° C. or greater, or any ranges or values therebetween.

In one aspect, a microorganism and/or enzyme produced by the microorganism may be tolerant to elevated pressure of about 0.5 MPa or greater, such as about 1 MPa or greater, such as about 5 MPa or greater, such as about 10 MPa or greater, such as about 15 MPa or greater, such as about 20 MPa or greater, such as about 30 MPa or greater, such as about 40 MPa or greater, such as about 50 MPa or greater, such as about 60 MPa or greater, such as about 70 MPa or greater, such as about 80 MPa or greater, such as about 90 MPa or greater, such as about 100 MPa or greater, such as about 150 MPa or greater, such as about 200 MPa or greater, such as about 250 MPa or greater, such as about 300 MPa or greater, such as about 350 MPa or greater, such as about 400 MPa or greater, such as about 450 MPa or greater, such as about 500 MPa or greater, such as about 550 MPa or greater, such as about 600 MPa or less, or any ranges or values therebetween.

Of course, combinations of extreme conditions as well as modifications of conditions during a depolymerization component of a process are encompassed herein. By way of example, a post-consumer product may begin to degrade upon contact with a low-saline environment. Following a period of time in a low-saline environment, the post-consumer product can be placed into a high-salinity environment that includes a high-salt tolerant microorganism (or enzyme expressed therefrom) and the degradation process can be completed. Similarly, a post-consumer product may begin to degrade in a relatively low temperature environment. Following a period of time, the product may then be placed into a high-temperature environment that includes a high-temperature tolerant microorganism (or enzyme expressed therefrom) and the degradation process can be completed.

In one aspect, an extremophilic enzyme for use in disclosed methods and processes can be a thermophilic enzyme that exhibits a $T_{opt}$ (that at which a maximum reaction rate can be achieved given suitable substrate) of about 40° C. or greater, about 50° C. or greater, about 60° C. or greater, about 70° C. or greater, about 80° C. or greater, or about 90° C. or greater in some aspects. Exemplary thermophiles (and thermophilic enzymes produced thereby, accession numbers for same provided in parenthesis in the provided listings) encompassed herein can include, without limitation, *Alicyclobacillus pomorum* (WP-084453829), *Amycolatopsis thermoflava* (WP-123687648), *Amycolatopsis thermalba* (WP-094002797), *Amycolatopsis rumanii* (WP-116109633), *Azospirillum thermophilum* (WP-109324320), *Deinococcus actinosclerus* (WP-082689076), *Fervidobacterium gondwanense* (SHN54810), *Gandjariella thermophila* (WP-137812779), *Georgenia satyanarayanai* (WP-146237554), *Hyphomanas* sp. (HAO37884), *Lihuaxuella thermophila* (WP-089972404), *Microbulbifer thermotolerans* (P-197462976), *Minwuia thermotolerans* (WP-206420073), *Rhodopseudomonas thermotolerans* (WP-114356866), *Rhodopseudomonas pentothenatexigens*, (WP-114356866), *Streptomyces thermovulgaris* (WP-067396676), *Thermanaeromonas toyohensis* (WP-084666479), *Thermoactinomyces* sp. CICC 10523 (WP-198056464), *Thermoactinomyces daqus* (WP-033100012), *Thermoactinospora* sp. (NUT44302), *Thermoactinospora rubra* (WP-084965756), *Thermobifida halotolerans* (WP-068692693), *Thermobifida fusca* (WP-011290529), *Thermobispora bispora* (WP-206206594), *Thermocatellispora tengchongensis*, (WP-185055796), *Thermochromatium tepidum* (WP-153975900), *Thermocrispum municipal* (WP-028851041), *Thermoflavimicrobium dichotomicum* (WP-093229000), *Thermogemmatispora carboxidivorans* (WP-081839208), *Thermogemmatispora aurantia* (WP-151728970), *Thermogemmatispora tikiterensis* (WP-11243376), *Thermogemmatispora onikobensis* (WP-084659191), *Thermoleophilaceae bacterium* (MBA2429278), *Thermomonospora echinospora* (WP-160147065), *Thermomonospora cellulosilytica* (WP-182704610), *Thermomonospora amylolytica* (WP-198679325), *Thermostaphylospora chromogena* (WP-093263254), *Thermus thermophilus* (WP-197735236), *Thermus aquaticus* (WP-053768217), *Thermus islandicus* (HEO42284).

Temperature-based enzymes encompassed herein are not limited to high temperature thermophilic enzymes (and their expressing microorganisms), and, in one aspect low temperature cryophilic enzymes (also referred to a psychrophilic enzymes), or an expressing microorganism, can be utilized. For instance, many bacterial strains will fail to multiply, but will still survive upon exposure to a temperature of about 10° C. for a period of time of about 6 hours. Thus, in some aspects, a microorganisms (or a cryophilic enzyme expressed therefrom) capable of activity at a temperature of about 10° C. or less, for instance 7° C. or less, or from about −15° C. to about 10° C. in some aspects, can be utilized. Exemplary psychrophiles encompassed herein can include, without limitation, *Alteromonas oceani* (WP-123325050), *Alteromonas alba* (WP-105936495), *Alteromonas* sp. 38 (WP-201299304), *Alteromonas macleodii* (WP-156078157), *Alteromonas ponticola* (WP-169211550), *Alteromonas lipolytica* (WP-070178363), *Arthrobacter crystallopoietes* (WP-005270754), *Bosea psychrotolerans* (WP-181011807), *Glaciecola amylolytica* (WP-164472126), *Hyphomonas* sp. (HAO37884), *Janthinobacterium psychrotolerans* (WP-065307954), *Massilia psychrophile* (WP-099914383), *Paraglaciecola psychrophile* (WP-007642709), *Polaromonas* sp. SP1 (WP-164483751), *Polaromonas* sp. AER18D-145 (WP-096697750), *Polaromonas* sp. CF318 (WP-007872516), *Polaromonas vacu-* olate (WP-168920719), *Polaromonas naphthalenivorans* (WP-157040436), *Polaromonas* sp. JS666 (WP-011482994), *Polaromonas glacialis* (WP-084181426), *Polaromonas* sp. EUR3 1.2.1 (WP-197028649), *Polaromonas* sp. CG_9.2 (WP-196864241), *Polaromonas* sp. CG_9.11 (WP-196869863), *Polaromonas eurypsychrophila* (WP-188708524), *Polaromonas* sp. (MBC7445758), *Polaromonas jejuensis* (WP-068832216), *Polaromonas* sp. AET17H-212 (WP-096671180), *Polaromonas* sp. YR568 (WP-092127764), *Polaromonas* sp. C04 (WP-077562980), *Pseudorhodobacter psychrotolerans* (WP-08235149), *Psychrobacillus lasiicapitis* (WP-142537823), *Psychrobacillus* sp. OK032 (WP-093265425), *Psychrobacillus* sp. OK028 (WP-093060398), *Psychrobacillus* sp. FJAT-21963 (WP-056833301), *Psychrobacter jeotgali* (WP-201583776), *Psychrobacter* sp. H8-1 (WP-201574875), *Psychrobacter* sp. Cmf 22.2 (WP-075103245), *Psychrobacter* sp. ENNN9_III (WP-058368887), *Psychrobacter* sp. P2G3 (WP-068327306), *Psychrobacter* sp. P11G5 (WP-068035467), *Psychrosphaera haliotis* (WP-155693683), *Shewanella psychrophile* (WP-077755816), *Simplicispira psychrophile* (WP-051603004), *Sphingobium psychrophilum* (WP-169570392), *Sphingomonas psychrolutea* (WP-188445826), *Clostridium homopropionicum* (WP-074782965), *Clostridium* sp. DL-VIII (WP-009169886), *Clostridium clostridioforme* CAG: 132 (CDB63357), *Zunongwangia atlantica* 221114-10F7 (ORL47196).

Extremophilic enzymes produced by halophiles can be utilized in some aspects. Exemplary halophiles (and halophilic enzymes produced thereby) encompassed herein can include, without limitation, *Alteromonas halophila* (WP-189403400), *Arthrobacter crystallopoietes* (WP-005270754), *Arthrobacter* sp. NEB 688 (WP-173027059), *Azospirillum halopraeferens* (WP-029007775), *Empedobacter haloabium* (TXE30443), *Desulfovibrio sulfodismutans* (NDY59052), *Halobacillus hunanensis* (WP-139377117), *Halobacillus ihumii* (WP-16352794), *Halobacteriovorax marinus* (WP-157868258), *Haloechinothrix halophila* (WP-051400222), *Halomarina oriensis* (WP-158204529), *Halomonas cerina* (WP-183325502), *Halomonas korlensis* (WP-089794761), *Halomonas* sp. PR-M31 (WP-048308188), *Halomonas aquamarine* (WP-089674669), *Halomonas zhanjiangensis* (WP-040460201), *Halomonas aestuarii* (WP-071946866), *Halomonas endophytica* (WP-102654199), *Halomonas heilongjiangensis* (WP-102629242), *Halomonas campaniensis* (WP-088701082), Halomonas alkaliphile (WP-038486873), Halomonas sp. ALS9 (WP-064233856), *Halomonas* sp. GFAJ-1 (WP-009098816), *Halomonas* sp. KHS3 (WP-041159480), *Halomonas alkaliphile* (WP-162218603), *Halomonas* sp. ZH2S (WP-160419650), *Halomonas alkaliantarctica* (WP-133732469), *Halomonas zincidurans* (WP-031384106), *Halomonas chromatireducens* (WP-083517585), *Halomonas* sp. KO116 (WP-035563078), *Halmonas* sp. A40-4 (WP-199285424), *Halomonas ventosae* (WP-035579360), *Halomonas* sp. HAL1) WP-008958555), *Halomonas* sp. MES3-P3E (WP-101146070), *Halomonas* sp. 1513 (WP-083700770), *Halomonas* sp. GT (WP-083007892), *Halomonas* sp. PA5 (QJQ97022), *Halomonas songnenensis* (WP-106373458), *Halomonas subglaciescola* (WP-079553041), *Halomonas* sp. HL-92 (WP-074398447), *Halomonas xinjiangensis* (WP-197053288), *Halomonas saliphila* (WP-104202516), *Halomonas* sp. HL-48 (WP-027336292), *Halomonas qijiaojingensis* (WP-189471950), *Halomonas urumqiensis* (WP-102588859), *Halomonas lutea* (WP-019020614), *Halomonas lutescens* (WP-188638020), *Halomonas salicampi* (WP-179930793), *Halomonas* sp. FME66 (WP-193092800), *Halomonas* sp. 156 (CAD5269671), *Halomonas* sp. L5 (WP-149329933), *Halomonas nanhaiensis* (WP-127060197), *Halomonas titanicae* (WP-144810212), *Halomonas* sp. SH5A2 (WP-186255949), *Halomonas* sp. TD01 (WP-009722522), *Halomonas* sp. PC (WP-127040515), *Halomonas* sp. RC (WP-126951333), *Halomonas* sp. DQ26W (WP-114573011), *Halomonas* sp. TQ8S (WP-114486842), *Halomonas* sp. PYC7W (WP-114478819), *Halomonas* sp. LBP4 (WP-181421925), *Halomonas* sp. QX-1 (WP-176303735), *Halomonas* sp. QX-2 (WP-180092182), *Halomonas glaciei* (WP-179915254), *Halomonas zhaodongensis* (WP-179927495), *Halomonas xianhensis* (WP-092845804), *Halomonas gudaonensis* (WP-089686750), *Halomonas humidisoli* (WP-095603093), *Halomonas boliviensis* (WP-083825729), *Halomonas* sp. QHL1 (WP-083571058), *Halomonas ilicicola* (WP-072822829), *Halomonas saccharevitans* (WP-089847692), *Halomonas muralis* (WP-089729617), *Halomonas arcis*(WP-089706930), *Halomonas boliviensis* (WP-040480056), *Halomonas andesensis* (WP-126944084), *Halomonas* sp. G5-11 (WP-168017113), *Halomonas* sp. THAF5a (QFU03326), *Halomonas taeanensis* (SDG32001), *Halorussus* sp. RC-68 (WP-128475846), *Halorussus ruber* (WP-135825713), *Halorussus* sp. ZS-3 (WP-158056449), *Halorussus* sp. HD8-83 (WP-135830119), *Halorussus salinus* (WP-135854680), *Halorussus amylolyticus* (WP-132060623), *Halorussus* sp. MSC15.2 (WP-163523881), *Haloterrigena limicola* (WP-008010666), *Haloterrigena hispanica* (WP-149782231), *Haloterrigena* sp. H1 (WP-138782397), *Isoptericola halotolerans* (WP-171781920), *Marinobacter* sp. X15-166B (WP-198929205), *Marinobacter* sp.LPB0319 (WP-2066439888), *Marinobacter salaries* (WP-126811858), *Marinobacter* sp. PJ-16 (WP-137435339), *Marinobacter nanhaiticus* (WP-004579452), *Marinobacter bohaiensis* (WP-111497193), *Marinobacter* sp. ANT_B65 (WP-202971753), *Marinobacter sediminum* (WP-203299860), *Marinobacter fonticola* (WP-148861082), *Marinobacter* sp. JB02H27 (WP-150989051), *Marinobacter maritimus* (WP-144775354), *Marinobacter nitratireducens* (WP-036130189), *Marinobacter aromaticivorans* (WP-100686899), *Marinobacter* sp. MCTG268 (WP-081899301), *Marinobacter profundi* (WP-099614009), *Marinobacter* sp. R17 (WP-123633665), *Marinobacter* sp. F3R11 (WP-113816648), *Marinobacter lipolyticus* (WP-012136507), *Marinobacter* sp. LV10MA510-1 (WP-098421792), *Marinobacter* sp. LV10R520-4 (WP-143751449), *Marinobacter antarcticus* (WP-072795398), *Marinobacter zhejiangensis* (WP-092022278), *Marinobacter* sp. LZ-8 (WP-138439039), *Marinobacter* sp. LZ-6 (WP-138437074), *Marinobacter* sp. DS40M8 (WP-169052525), *Marinobacter shengliensis* (WP-106694886), *Marinobacter algicola* (WP-007152654), *Marinobacter salicampi* (WP-166253549), *Marinobacter* sp. JSM 1782161 (WP-165857264), *Methyloligella halotolerans* (WP-069095898), *Micromonospora halophytica* (WP-091291516), *Natronococcus* sp. LS1_42 (WP-148858780), *Nocardiopsis halotolerans* (WP-017570132), *Paracoccus halophilus* (WP-036743786), *Roseivivax halodurans* (WP-037257008), *Saccharomonospora halophila* (WP-157601674), *Shewanella vesiculosa* (NCO72699), *Shewanella psychrophila* (WP-077755816), *Shewanella frigidimarina* (WP-123883413), *Shewanella khirikhana* (WP-126168307), *Shewanella halifaxensis* (WP-108946642), *Shewanella waksmanii* (WP-028774143), *Shewanella saliphila* (WP-188922486), *Shewanella ulleungensis* (WP-188954542), *Shewanella litoralis* (WP-160052797).

Extremophilic enzymes produced by acidophiles can be utilized in some aspects. For instance, acidophilic enzymes that exhibit activity at a pH of from about 1 to about 5.5 can be utilized. Exemplary acidophiles (and acidophilic enzymes produced thereby) encompassed herein can include, without limitation, *Acidibrevibacterium fodinaquatile* (WP-162800754), *Acidicaldus* sp (HGC43174), *Acidiphilium cryptum* (WP-050751056), *Acidisphaera rubrifaciens* (WP-084623200), *Acidisphaera* sp. S103 (WP-158926549), *Acidobacteria bacterium* (MBI4850940), *Acidobacteriales bacterium* (MBA3914351), *Acidimicrobiaceae bacterium* (TPW09344), *Acidothermus cellulolyticus* (WP-011719018), *Acidovorax* sp. (RZJ59385), *Acidovorax* sp. Leaf160 (WP-156382378), *Acidovorax citrulli* (WP-116212334), *Acidovorax* sp. ST3 (WP-110960035), *Acidovorax* sp. SD340 (WP-055393692), *Acidovorax* sp. JHL-9 (WP-026434583), *Acidovorax* sp. JHL-3 (WP-024815995), *Acidovorax* sp. 59 (WP-099731663), *Acidovorax* sp. T1 (WP-087747071), *Acidovorax radices* (WP-145694120), *Acidovorax citrulli* (MVT28077), *Acidovorax konjaci* (WP-184273732), *Acidovorax* sp. YL-MeA13-2016 (WP-179683865), *Acidovorax* sp. JMULE5 (WP-176888736), *Acidovorax carolinensis* (WP-086926820), *Acidovorax* sp. Root219 (WP-057264729), *Acidovorax* sp. Root217 (WP-057200451), *Acidovorax* sp. Root70 (WP-056639581), *Acidovorax* sp. Root267 (WP-057271450), *Acidovorax* sp. Root275 (WP-057228519), *Acidovorax* sp. Root568 (WP-056742554), *Acidovorax* sp. Root402 (WP-056056880), *Acidovorax* sp. Leaf78 (WP-056167938), *Acidovorax* sp. CF316 (WP-007848954), *Acidovorax* sp. NO-1 (WP-008904688), *Acidovorax* sp. KKS102 (WP-015015374), *Acidovorax* sp. BoFeN1 (WP-114656624), *Acidovorax* sp. MR-S7 (WP-020227330), *Acidovorax* sp. GW101-3H11 (WP-063462297), *Acidovorax* sp. 100 (WP-121942233), *Acidovorax* sp. 94 (WP-121421729), *Acidovorax* sp. 93 (WP-121508058), *Acidovorax* sp. IB03 (WP-198847087), *Acidovorax facilis* (WP-182119389), *Acidovorax cattleya* (WP-196290774), *Acidovorax soli* (WP-184855240), *Acidovorax* sp. TP4 (BAA35137), *Acidovorax* sp. HMWF018 (WP-199227795), *Acidovorax* sp. 107 (WP-108624875), *Acidovorax* sp. 69 (WP-100412617), *Acidovorax* sp. RAC01 (WP-069104250), *Acidovorax avenae* (WP-107129247), *Acidovorax* sp. ACV01 (WP-192426852), *Acidovorax* sp. ACV02 (WP-192419383), *Acidovorax* sp. SRB_14 (WP-173025722), *Acidovorax* sp. 99 (WP-116748450), *Acidovorax delafieldii* (WP-060985808), *Acidovorax* sp. 16-35-5 (WP-175506463), *Acidovorax valerianellae* (WP-092740663), *Acidovorax temperans* (WP-142084895), *Acidovorax oryzae* (WP-026433360), *Acidovorax* sp. SRB_24 (WP-169168665), *Acidovorax cavernicola* (WP-119555154), *Acidovorax temperans* (WP-044398345), *Acidisoma* sp. S159 (WP-159014448), *Acidisoma* sp. L85 (WP-158802619), Acidisphaera sp. L21 (WP-158747166), Acidiphilium cryptum JF-5 (ABQ28771), *Actinospica acidiphila* (WP-193455356), *Alicyclobacillus pomorum* (WP-084453829), *Amycolatopsis acidiphila* (WP-144638401), *Azospirillum baldaniorum* (WP-014240680), *Bacillus megaterium* (WP-013057692), *Catenulispora acidiphila* (WP-015793547), *Delftia* sp. UME58 (WP-183018265), *Delftia acidovorans* (WP-202760212), *Delftia lacustris* (WP-016453321), *Methylocapsa acidiphila* (WP-026607232), *Paraburkholderia acidophila* (WP-084908171), *Paraburkholderia acidisoli* (WP-158957882), *Paraburkholderia acidipaludis* (WP-027796272), *Priestia megaterium* (WP-016764703), *Rhizobium acidisoli* (WP-054183259), *Rhodoblastus acidophilus* (WP-088519736), *Stenotrophomonas acidaminiphila* (WP-054666853), *Streptomyces acidiscabies* (WP-078480871), *Streptomyces acidicola* (WP-152864677).

Extremophilic enzymes produced by alkaliphiles can be utilized in some aspects. For instance, alkaliphilic enzymes that exhibit activity at a pH of from about 7.5 to about 11.5) can be utilized. Exemplary alkaliphiles (and alkaliphilic enzymes produced thereby) encompassed herein can include, without limitation, *Alkalilacustris brevis* (WP-114966465), *Alkalihalobacillus macyae* (WP-152670966), *Alkalihalobacillus pseudofirmus* (WP-012960136), *Alkalihalobacillus shacheensis* (WP-082676287), *Alkalihalobacillus xiaoxiensis* (WP-204463621), *Alkalilimnicola* sp. S0819 (WP-152144452), *Alkalimonas amylolytica* (WP-091344878), *Amycolatopsis alkalitolerans* (WP-139096058), *Cupriavidus alkaliphilus* (WP-111516860), *Ensifer alkalisoli* (WP-151613639), *Lacimicrobium alkaliphilum* (WP-062478888), *Lysobacter alkalisoli* (QDH70273), *Massilia alkalitolerans* (WP-036214799), *Methylobacter* sp. B2 WP-174627553), *Neorhizobium alkalisoli* (WP-105385441), *Nocardiopsis alkaliphile* (WP-051045978), *Ramlibacter alkalitolerans* (WP-201687394), *Spinactinospora alkalitolerans* (WP-179641803).

Extremophilic enzymes produced by piezophiles can be utilized in some aspects. For instance, piezophilic enzymes that exhibit activity at a pressure of about 110 kPa or greater, or about 50 MPa or greater in some aspects, can be utilized. Exemplary piezophiles (and piezophilic enzymes produced thereby) encompassed herein can include, without limitation, *Oceanobacillus piezotolerans* (WP-121525044), *Oceanobacillus profunda* (WP-169713018), *Colwellia marinimaniae* (WP-082606415), *Salinimonas sediminis* (WP-108566897).

Radiation resistant extremophiles are also encompassed herein. For instance radiation resistant organisms such as *Deinococcus radiotolerans* which produces a radiation resistant enzyme (WP_189068351) can be utilized. A radiation resistant organism and radiation resistant enzyme encompassed herein can generally be active at a level of acute ionizing radiation (gamma rays, high energy UV rays, X-rays, etc.) of about 1000 Gy or greater, or about 2000 Gy or greater in some aspects.

In one aspect, extremophilic depolymerase enzyme or extremophilic microorganism for use as disclosed herein can include polyextremophiles that exist at a combination of extreme environmental conditions. For example, a halophilic alkalithermophile, which ideally exist at both high saline and alkaline conditions, or a psychrotrophic halophile, which ideally exist at both low temperature and high saline conditions. Most of the piezophilic (pressure-loving) extremophiles are found at the bottom of the ocean and are therefore also halophilic (salt-loving) and psychrophilic (cold-loving), all of which are conditions that can be simultaneously generated and maintained within a reaction chamber to provide mesophilic pathogen decontamination in conjunction with depolymerization and production of HA monomer. In such an aspect, mesophilic contamination can be addressed through multiple mechanisms in conjunction with a depolymerization reaction catalyzed by a single polyextremophilic enzyme.

Exemplary polyextremophiles (and polyextremophilic enzymes produced thereby) encompassed herein can include, without limitation (some of which are also included in those referred to previously), *Acidothermus cellulolyticus* (WP_011719018), *Arthrobacter crystallopoietes* (WP_005270754), *Arthrobacter* sp. NEB 688 (WP_173027059), *Amycolatopsis decaplanina*

(WP_007028471), *Amycolatopsis azurea* (WP_039919726), *Amycolatopsis orientalis* (WP_044853678), *Amycolatopsis regifaucium* (WP_061985795), *Amycolatopsis alba* (WP_020632115), *Amycolatopsis* sp. CB00013 (WP_073845662), *Amycolatopsis* sp. WAC 04182 (WP_125683401), *Amycolatopsis* sp. WAC 04197 (WP_125733174), *Amycolatopsis* sp. WAC 01416 (WP_125797595), *Amycolatopsis lurida* (WP_034314791), *Amycolatopsis australiensis* (WP_072479564), *Amycolatopsis* sp. WAC 01375 (WP_125786221), *Amycolatopsis* sp. YIM 10 (WP_194239921), *Amycolatopsis australiensis* (WP_072480012), *Amycolatopsis* sp. WAC 01376 (WP_125797552), *Amycolatopsis* sp. WAC 01376 (WP_125791151), *Amycolatopsis* sp. BJA-103 (WP_168214428), *Amycolatopsis* sp. WAC 04169 (WP_125694889), *Amycolatopsis* sp. YIM 10 (WP_153034611), *Amycolatopsis xylanica* (WP_091289432), *Amycolatopsis thailandensis* (WP_093938547), *Amycolatopsis tolypomycina* (WP_091314877), *Amycolatopsis* (WP_094002797), *Amycolatopsis mediterranei* (WP_013227677), *Amycolatopsis tolypomycina* (WP_091316988), *Amycolatopsis mediterranei* (WP_013225900), *Amycolatopsis* sp. MJM2582 (WP_037335097), *Amycolatopsis pretoriensis* (WP_086680613), *Amycolatopsis mediterranei* (WP_014467631), *Amycolatopsis mediterranei* (WP_013227743), *Amycolatopsis lexingtonensis* (WP_086861387), *Amycolatopsis balhimycina* (WP_026468360), *Amycolatopsis tolypomycina* (WP_091309318), *Amycolatopsis mediterranei* (WP_013225589), *Amycolatopsis lexingtonensis* (WP_086864508), *Amycolatopsis balhimycina* (WP_020640708), *Amycolatopsis balhimycina* (WP_020639925), *Amycolatopsis japonica* (WP_038521005), *Amycolatopsis vancoresmycina* (WP_051767789), *Amycolatopsis vancoresmycina* (WP_162146255), *Amycolatopsis vancoresmycina* (WP_003055279), *Amycolatopsis vancoresmycina* (WP_003059137), *Amycolatopsis arida* (WP_177216885), *Amycolatopsis orientalis* (WP_037305638), *Amycolatopsis mediterranei* U32 (ADJ49174), *Amycolatopsis balhimycina* (WP_020640186), *Amycolatopsis balhimycina* (WP_020646797), *Amycolatopsis regifaucium* (WP_158070237), *Amycolatopsis umgeniensis* (WP_184896802), *Amycolatopsis mediterranei* (WP_176742238), *Amycolatopsis orientalis* (WP_037318494), *Amycolatopsis taiwanensis* (WP_027941815), *Amycolatopsis thermoflava* (WP_037323546), *Amycolatopsis nigrescens* (WP_157357235), *Amycolatopsis benzoatilytica* (WP_020658806), *Amycolatopsis thermoflava* (WP_123687648), *Amycolatopsis* sp. MtRt-6 (WP_206788940), *Amycolatopsis nigrescens* (WP_020673950), *Amycolatopsis* sp. MtRt-6 (WP_206796628), *Amycolatopsis* sp. MtRt-6 (WP_206785025), *Amycolatopsis* sp. 195334CR (WP_206808196), *Amycolatopsis* sp. SID8362 (WP_166641473), *Amycolatopsis vastitatis* (WP_167441766), *Amycolatopsis* sp. MtRt-6 (WP_206794433), *Amycolatopsis* sp. 195334CR (WP_206804625), *Amycolatopsis* sp. SID8362 (WP_160695402), *Amycolatopsis* sp. 195334CR (WP_206805671), *Amycolatopsis mediterranei* S699 (AEK42609), *Amycolatopsis* sp. SID8362 (WP_160697844), *Amycolatopsis ruanii* (WP_116109633), *Amycolatopsis vastitatis* (WP_093953441), *Amycolatopsis antarctica* (WP_094864937), *Amycolatopsis* sp. SID8362 (WP_160697847), *Amycolatopsis vastitatis* (WP_093953193), *Amycolatopsis rifamycinica* (WP_043779284), *Amycolatopsis rifamycinica* (WP_043787922), *Amycolatopsis orientalis* (WP_044854926), *Amycolatopsis albispora* (WP_113697064), *Amycolatopsis vastitatis* (WP_093953762), *Amycolatopsis keratiniphila* (WP_043848437), *Amycolatopsis rifamycinica* (WP_043776526), *Amycolatopsis* sp. ATCC 39116 (WP_039791697), *Amycolatopsis* sp. CA-126428 (WP_199191631), *Amycolatopsis* sp. CA-128772 (WP_199199004), *Amycolatopsis rifamycinica* (WP_043775110), *Amycolatopsis* sp. CA-128772 (WP_103347542), *Amycolatopsis* sp. CA-126428 (WP_103341161), *Amycolatopsis* sp. CA-126428 (WP_103338297), *Amycolatopsis* sp. CA-128772 (WP_103347494), *Amycolatopsis* sp. CA-128772 (WP_103351389), *Amycolatopsis* sp. CA-126428 (WP_10334050), *Amycolatopsis* sp. CA-126428 (WP_103337215), *Amycolatopsis* sp. BJA-103 (WP_101611121), *Amycolatopsis rifamycinica* (WP_043775220), *Amycolatopsis bullii* (WP_191309718), *Amycolatopsis alkalitolerans* (WP_139096058), *Amycolatopsis* sp. CA-126428 (WP_103340450), *Amycolatopsis* sp. A23 (WP_155542679), *Amycolatopsis* sp. A23 (WP_155546301), *Amycolatopsis bullii* (WP_191313482), *Amycolatopsis oliviviridis* (WP_191256639), *Amycolatopsis bullii* (WP_191317041), *Amycolatopsis* sp. A23 WP_155546374), *Amycolatopsis bullii* (WP_191309628), *Amycolatopsis* sp. H6 (2020) (MBE8525409), *Amycolatopsis* sp. H6 (2020) (MBE8516875), *Amycolatopsis acidiphila* (WP_144638401), *Amycolatopsis deserti* (WP_191242759), *Amycolatopsis* sp. H6 (2020) (MBE8523464), *Amycolatopsis roodepoortensis* (WP_192744003), *Amycolatopsis lexingtonensis* (WP_086861614), *Amycolatopsis* sp. H6 (2020) (MBE8523449), *Amycolatopsis lexingtonensis* (WP_086861672), *Amycolatopsis* sp. H6 (2020) (MBE8519699), *Amycolatopsis eburnean* (WP_125314097), *Amycolatopsis* sp. PIP199 (WP_181777181), *Amycolatopsis eburnean* (WP_125313793), *Amycolatopsis* sp. YIM 10 (WP_153034239), *Amycolatopsis rhizosphaerae* (WP_144585784), *Amycolatopsis ebumean* (WP_191984376), *Amycolatopsis australiensis* (WP_072479963), *Amycolatopsis ebumean* (WP_125313723), *Amycolatopsis* sp. Hca4 (WP_176178332), *Amycolatopsis pretoriensis* (WP_086674376), *Amycolatopsis* sp. YIM 10 (WP_153033440), *Amycolatopsis* sp. Hca4 (WP_176171164), *Amycolatopsis thermalba* (WP_115944128), *Amycolatopsis tolypomycina* (WP_091313624), *Amycolatopsis sacchari* (WP_09150482), *Amycolatopsis kentuckyensis* (WP_086849953), *Amycolatopsis pretoriensis* (WP_086676731), *Amycolatopsis kentuckyensis* (WP_086838850), *Amycolatopsis vancoresmycina* (WP_033262149), *Amycolatopsis sacchari* (WP_091509483), *Amycolatopsis eburnean* (RSD12104), *Amycolatopsis vancoresmycina* (WP_033262457), *Amycolatopsis tolypomycina* (WP_091314771), *Amycolatopsis kentuckyensis* (WP_086842561), *Amycolatopsis tolypomycina* (SED02538), *Amycolatopsis kentuckyensis* (WP_086850817), *Amycolatopsis keratiniphila* (SDU59319), *Amycolatopsis* sp. SID8362 (NBH10816), *Amycolatopsis sacchari* (SFI91313), *Amycolatopsis keratiniphila* (AGM10176), *Amycolatopsis vancoresmycina* DSM 44592 (EOD69417), *Amycolatopsis vancoresmycina*

DSM 44592 (EOD63279), *Colwellia psychrerythraea* (WP_033095470), *Colwellia psychrerythraea* (WP_033082346), *Colwellia chukchiensis* (WP_085285385), unclassified *Colwellia* (WP_182245161), unclassified *Colwellia* (WP_108456828), *Colwellia* (WP_082606415), unclassified *Colwellia* (WP_182136131), unclassified *Colwellia* (WP_182222214), *Colwellia psychrerythraea* (WP_138140233), unclassified *Colwellia* (WP_182213899), unclassified *Colwellia* (WP_182191078), *Colwellia psychrerythraea* (WP_033082290), *Colwellia* sp. Arc7-635 (WP_126668020), *Colwellia aestuarii* (WP_143323591), *Colwellia* sp. BRX8-4 (WP_182258889), *Colwellia* sp. (MBL4900302), *Colwellia* sp. (MBL0710453), *Colwellia* sp. PAMC 21821 (WP_081180401), *Colwellia* sp. (MBL4764635), *Colwellia* sp. 12G3 (WP_101233926), *Colwellia Polaris* (WP_085306422), *Colwellia* sp. Bg11-28 (WP_157825823), *Colwellia* sp. BRX10-3 (WP_182133028), *Colwellia* sp. MB02u-6 (WP_182233718), *Colwellia* sp. BRX8-2 (WP_182231462), *Colwellia* sp. MB3u-4 (WP_182185277), *Colwellia* sp. BRX9-1 (WP_182230151), *Colwellia* sp. BRX8-7 (WP_182242732), *Colwellia* sp. (NQZ90610), *Colwellia* sp. MB02u-10 (WP_182238471), *Colwellia* sp. (NQZ28611), *Colwellia* sp. (QY47923), *Colwellia* sp. Bg11-12 (WP_182229555), *Colwellia* sp. (NQY89088), *Colwellia beringensis* (WP_081152231), *Colwellia* sp. (NQZ82584), *Colwellia demingiae* (WP_146789187), *Candidatus Colwellia aromaticivorans* (WP_114327742), *Colwellia* sp. MB02u-9 (WP_182197537), *Colwellia mytili* (WP_085299583), *Colwellia* sp. (NQY47915), *Colwellia* sp. (NQZ28619), *Haladaptatus paucihalophilus* (WP_007977720), *Haladaptatus litoreus* (WP_076429835), *Haladaptatus paucihalophilus* (WP_007977722), *Haladaptatus* sp. R4 (WP_066143160), *Haladaptatus cibarius* (WP_049970104), *Haladaptatus* sp. (W1 WP_069450211), *Haladaptatus cibarius* (WP_049971911), *Haladaptatus paucihalophilus* DX253 (SHK49397), *Halobacillus ihumii* (WP_163527944), *Halobacillus hunanensis* (WP_139377117), *Halomarina oriensis* (WP_124957125), *Halomarina oriensis* (WP_158204529), *Halomonas* (*ventosae*) (WP_035579360), *Halomonas* sp. 156 (CAD5269671), unclassified *Halomonas* (WP_008956714), *Halomonas* (WP_035577590), *Halomonas chromatireducens* (WP_083517585), *Halomonas meridiana* (WP_083602247), unclassified *Halomonas* (sp. HL-92) (WP_074398447), *Halomonas* sp. GFAJ-1 (WP_009101808), *Halomonas chromatireducens* (WP_066448186), *Halomonas* sp. KO116 (WP_035563078), *Halomonas* sp. KO116 (WP_035565981), *Halomonas arcis* (WP_089708323), *Halomonas* sp. TD01 (WP_009724586), *Halomonas arcis* (WP_089706930), *Halomonas korlensis* (WP_089792833), *Halomonas alkaliantarctica* (WP_133732469), *Halomonas ilicicola* (WP_072822829), *Halomonas boliviensis* (WP_007114283), *Halomonas* sp. HL-48 (WP_027336292), *Halomonas alkaliphila* (WP_038486873), unclassified *Halomonas* (WP_074394764), *Halomonas* sp. HAL1 (WP_008958555), *Halomonas subglaciescola* (WP_079553041), *Halomonas korlensis* (WP_089797758), *Halomonas cerina* (WP_183325502), unclassified *Halomonas* (sp. RC) (WP_126951333), *Halomonas* sp. TD01 (WP_009722522), *Halomonas titanicae* (WP_089691351), *Halomonas aquamarine* (WP_089674669), *Halomonas gudaonensis* (WP_089686750), *Halomonas alkaliantarctica* (WP_133731111), *Halomonas saccharevitans* (WP_089847692), *Halomonas xianhensis* (WP_092845804), *Halomonas songnenensis* (WP_106373458), *Halomonas zincidurans* (WP_031384106), *Halomonas lutea* (WP_019020614), *Halomonas boliviensis* (WP_083825729), *Halomonas* sp. GFAJ-1 (WP_009098816), *Halomonas muralis* (WP_089729617), *Halomonas boliviensis* (WP_040480056), *Halomonas* sp. (HAA45741), *Halomonas zhanjiangensis* (WP_040460201), *Halomonas campaniensis* (WP_088701082), *Halomonas alkaliphile* (WP_162218603), *Halomonas* sp. ZH2S (WP_160419650), *Halomonas endophytica* (WP_102654199), *Halomonas* sp. ALS9 (WP_064233856), *Halomonas* sp. KHS3 (WP_041159480), *Halomonas salicampi* (WP_179930793), *Halomonas salicampi* (WP_179928774), *Halomonas heilongjiangensis* (WP_102629242), *Halomonas campaniensis* (WP_088701419), *Halomonas* sp. MES3-P3E (WP_101146070), *Halomonas alkaliantarctica* (WP_030070137), *Halomonas xinjiangensis* (WP_197053288), *Halomonas alkaliantarctica* (WP_030072571), *Halomonas* sp. GT (WP_083002052), *Halomonas* sp. A40-4 (WP_199285424), *Halomonas* sp. GT (WP_083007892), *Halomonas* sp. 1513 (WP_076746720), *Halomonas* sp. HL-48 (WP_027335517), *Halomonas* sp. 1513 (WP_083700770), *Halomonas* sp. (MBL1266350), *Halomonas urumqiensis* (WP_102588859), *Halomonas lutescens* (WP_188638020), *Halomonas lutescens* (WP_188638515), *Halomonas* sp. FME66 (WP_193092800), *Halomonas saliphila* (WP_104202516), *Halomonas* sp. (MBE0488383), *Halomonas qijiaojingensis* (WP_189471950), *Halomonas* sp. 3(2) (WP_151442249), *Halomonas* sp. FME20 (WP_192536925), *Halomonas* sp. SH5A2 (WP_186255949), *Halomonas* sp. TQ8S (WP_114486842), *Halomonas titanicae* (WP_144812651), *Halomonas* sp. PYC7W (WP_114478819), *Halomonas* sp. PYC7W (WP_114478692), *Halomonas* sp. LBP4 (WP_181421925), *Halomonas* sp. TQ8S (WP_114487405), *Halomonas glaciei* (WP_179915254), *Halomonas* sp. QX-29 (WP_180092182), *Halomonas* sp. SH5A2 (WP_186253301), *Halomonas zhaodongensis* (WP_179927495), *Halomonas titanicae* (WP_144810212), *Halomonas nanhaiensis* (WP_127060197), *Halomonas pantelleriensis* (WP_089659512), *Halomonas zhaodongensis* (WP_179926908), *Halomonas humidisoli* (WP_095603093), *Halomonas* sp. QHL1 (WP_083571058), *Halomonas* sp. PC (WP_127040515), *Halomonas* sp. DQ26W (WP_114573011), *Halomonas shengliensis* (WP_089679049), *Halomonas* sp. QX-1 (WP_176303735), *Halomonas* sp. QHL1 (WP_071693265), *Halomonas korlensis* (WP_089794761), *Halomonas aestuarii* (WP_071946866), *Halomonas* sp. PR-M31 (WP_048308188), *Halomonas* sp. PA5 (QJQ97022), *Halomonas andesensis* (WP_126944084), *Halomonas* sp. PA5 (QJQ94877), *Halomonas* sp. L5 (WP_149329933), *Halomonas korlensis* (SFU56513), *Halomonas* sp. G5-11 (WP_168017113), *Halomonas subterranean* (WP_092824778), *Halomonas* sp. (HDZ47214), *Halomonas* sp. THAF5a (QFU03326), *Halomonas* sp (HDZ46744), *Halomonas chromatireducens* (AMD02558), *Halomonas andesensis* (WP_126948398), *Halomonas korlensis* (SFU93166), *Halomonas taeanensis* (SDG32001), *Halorussus salinus* (WP_135854385), *Halorussus* sp. MSC15.2 (WP_163523881), *Halorussus salinus* (WP_135854680), *Halorussus amylolyticus* (WP_132060623), *Halorussus* sp. ZS-3 (WP_158056449), *Halorussus amylolyticus*

(WP_132060625), *Halorussus* sp. ZS-3 (WP_158056448), *Halorussus* sp. RC-68 (WP_128475846), *Halorussus ruber* (WP_135825713), *Halorussus ruber* (WP_135825712), *Halorussus* sp. HD8-83 (WP_135830119), *Marilnobacter* sp. LV10R520-4 (WP_143751449), *Marinobacter zhejiangensis* (WP_092022278), unclassified *Marilnobacter* (WP_150989051), *Marinobacter nitratireducens* (WP_036130189), *Marinobacter salaries* (WP_091640839), unclassified *Marilnobacter* (WP_098419392), *Marinobacter algicola* (WP_007152654), *Marinobacter antarcticus* (WP_072795398), unclassified *Marinobacter* (WP_152438805), *Marinobacter* (WP_075197007), *Marinobacter profundi* (WP_099614009), *Marinobacter* sp. LPB0319 (WP_206643988), *Marinobacter* sp. DS40M8 (WP_169052525), *Marinobacter* sp. X15-166B (WP_198929205), unclassified *Marilnobacter* (WP_081899301), *Marinobacter* sp. PJ-16 WP_137435339), *Marinobacter bohaiensis* (WP_111497193), *Marinobacter sediminum* (WP_203299860), *Marinobacter lipolyticus* (WP_012136507), *Marinobacter* sp. ANT_B65 (WP_202971753), *Marinobacter nanhaiticus* (WP_004579452), *Marinobacter salaries* (WP_126811858), *Marinobacter maritimus* (WP_144775354), *Marinobacter* sp. F3R11 (WP_113816648), *Marinobacter* sp. LZ-8 (WP_138439039), *Marinobacter* sp. LZ-6 (WP_138437074), *Marinobacter shengliensis* (WP_106694886), *Marinobacter fonticola* (WP_148861082), *Marinobacter* sp. JSM 1782161 (WP_165857264), *Marinobacter* sp. R17 (WP_123633665), *Marinobacter salicampi* (WP_166253549), *Marinobacter* sp. LV10MA510-1 (WP_098421792), *Thermobifida fusca* (WP_016187994), *Zunongwangia atlantica* 221114-10F7 (ORL471960).

Of course, any combination of microorganisms or enzymes therefrom can be utilized in disclosed methods and systems, and any combination of environmental conditions corresponding to active conditions for the enzymes can likewise be utilized to provide a multi-dimensional approach to simultaneous decontamination of a post-consumer product and degradation of PHA in the post-consumer product.

In addition to or alternative to microorganisms that naturally express one or more of the enzymes as may be useful in provide HA monomer from a post-consumer product, one or more genetically modified microorganisms may be used that can express an exogenous enzyme(s) capable of degrading a post-consumer product and producing HA monomer from PHA including in the product. For instance, genetically engineered PHADase variants can be recombined into a bacterial chromosome under native promotor and ribosomal binding site control. Such bacteria can then produce a desired PHADase variant, for instance in response to environmental conditions that can instigate PHA depolymerization, e.g., energy/carbon source depravation.

In general, any suitable organism can be modified to express a PHADase, for example from a constitutive vector coupled with the correct signal sequence. For instance, any suitable gram positive or gram negative bacterium can be used to produce and secrete a PHADase, which can be a gram positive PHADase. In this manner, an expression system can be customized based on, e.g., environmental variables of the depolymerization component, the type and amount of post-consumer materials to be processed, as well as combinations thereof. In addition, the sequence of the enzyme can be matched to the environment and/or the PHA to be processed by selecting one or more of approximately 6,400 depolymerase sequences that are known (e.g. NCBI database) or with a fully or partially engineered variant. In one aspect, an organism can be transformed with a plasmid vector that harbors a constitutively expressed gene in coding a PHADase that contains an appropriate N-ter signal sequence. Alternatively, an organism can have a depolymerase gene inserted into the chromosome by transduction, linear recombination, or any other suitable method.

An enzyme can be expressed by transformation of a suitable host organism by use of either prokaryotic or eukaryotic host cells. Examples of host cell types include, without limitation, bacterial cells (e.g., *E. coli*), yeast cells (e.g., *pichia*, *S. cerevisiae*), cultured insect cell lines (e.g., *Drosophila*), plant cell lines (e.g., maize, tobacco, rice, sugarcane, potato tuber), or mammalian cells lines (e.g., Chinese Hamster Ovary (CHO)). In one aspect, a recombinant host cell system can be used that processes and post-translationally modifies nascent polypeptides in a manner desired to produce the final catalytic enzyme.

However, any suitable organism can be utilized. For example, a suitable gram positive or gram negative bacteria may be used such as a bacteria obtained from the genus *Streptomyces*. Particular examples of microorganisms from the above genus include *Streptomyces thermovulgaris*, *Streptomyces thermoolivaceus*, *Streptomyces thermohygroscopicus*, *Streptomyces thermocarboxydovorans*, or mixtures thereof.

Other genera may further be used in accordance with the present disclosure to express modified enzymes including, without limitation, Firmicutes (*Bacillus*, *Lihuaxuella*, and *Clostridium*), Proteobacteria (*Bradyrhizobium*, *Sphingomonas*, *Azotobacter*, *Azospirillum*, *Nitrobacter*, *Lysobacter*, *Stenotrophomonas*, *Rhizobium*, *Acinetobacter*, *Thiobacillus*, *Schlegelella*, *Janthinobacterium*, *Sinorhizobium*, *Pseudomonas*, *Agrobacterium*, and *Escherichia* (e.g. *Escherichia coli*)), Actinobacteria (*Rhodococcus*, *Arthobacter*, *Streptomyces*, *Conexibacter*, *Rhodococcus*, *Solirubrobacter*, *Micrococcus*, *Rubrobacter*, and *Actinomyces*), Bacteroidetes (*Flavobacterium* and *Pedobacter*), Deinococcus-thermus (*Deinococcus* and *Thermus*), Gemmatimonadetes (*Gemmatimonas* and *Gemmatirosa*, (Spirochaetes (*Tumeriella* and *Leptospira*), Verrucomicrobia (*Pedosphaera*, *Chthoniobacter*, and *Verrucomicrobia*), Chloroflexi (*Thermogemmatispora* and Dictyobacter), and Armatimonadetes (*Fimbriimonas*).

A nucleic acid sequence that encodes an enzyme may be placed in an expression vector for expression in the host. Such expression vectors can generally comprise a transcriptional initiation region linked to the nucleic acid sequence that encodes the enzyme. An expression vector can also include a plurality of restriction sites for insertion of the nucleic acid to be under the transcriptional regulation of various control elements. The expression vector additionally may contain selectable marker genes. Suitable control elements such as enhancers/promoters, splice junctions, polyadenylation signals, etc. may be placed in close proximity to the coding region to permit proper initiation of transcription and/or correct processing of the primary transcript, i.e., the coding region for the enzyme. Alternatively, the coding region utilized in an expression vector may contain endogenous enhancers/promoters, splice junctions, intervening sequences, polyadenylation signals, etc., or a combination of both endogenous and exogenous control elements.

An expression vector generally includes in the 5'-3' direction of transcription, a promoter, a transcriptional and translational initiation region, a DNA sequence that encodes the enzyme, and a transcriptional and translational termination region functional in the host cell. In one aspect, a T7-based vector can be used, which can include at least the following components: an origin of replication, a selectable antibiotic resistance gene (e.g.—amp$^r$, tetr, chlrr), a multiple cloning site, T7 initiator and terminator sequences, a ribosomal binding site, and a T7 promoter.

In general, any suitable promoter may be used that is capable of operative linkage to the heterologous DNA such that transcription of the DNA may be initiated from the promoter by an RNA polymerase that may specifically recognize, bind to, and transcribe the DNA in an open reading frame. Some useful promoters include, constitutive promoters, inducible promoters, regulated promoters, cell specific promoters, viral promoters, and synthetic promoters. Moreover, while promoters may include sequences to which an RNA polymerase binds, this is not a requirement. A promoter may be obtained from a variety of different sources. For example, a promoter may be derived entirely from a native gene of the host cell, be composed of different elements derived from different promoters found in nature, or be composed of nucleic acid sequences that are entirely synthetic. A promoter may be derived from many different types of organisms and tailored for use within a given cell. For example, a promoter may include regions to which other regulatory proteins may bind in addition to regions involved in the control of the protein translation, including coding sequences.

A translation initiation sequence can be derived from any source, e.g., any expressed *E. coli* gene. Generally, the gene is a highly expressed gene. A translation initiation sequence can be obtained via standard recombinant methods, synthetic techniques, purification techniques, or combinations thereof, which are all well known. Alternatively, translational start sequences can be obtained from numerous commercial vendors. (Operon Technologies; Life Technologies Inc.).

The termination region may be native with the transcriptional initiation region, may be native with the coding region, or may be derived from another source. Transcription termination sequences recognized by the transformed cell are regulatory regions located 3' to the translation stop codon, and thus together with the promoter flank the coding sequence. Examples include transcription termination sequences derived from genes with strong promoters, such as the trp gene in *E. coli* as well as other biosynthetic genes.

Vectors that may be used include, but are not limited to, those able to be replicated in prokaryotes and eukaryotes. For example, vectors may be used that are replicated in bacteria, yeast, insect cells, and mammalian cells. Examples of vectors include plasmids, phagemids, bacteriophages, viruses (e.g., baculovirus), cosmids, and F-factors. Specific vectors may be used for specific cells types. Additionally, shuttle vectors may be used for cloning and replication in more than one cell type. Such shuttle vectors are known in the art. The vector may, if desired, be a bi-functional expression vector that may function in multiple hosts.

An expression vector that encodes a PHADase of interest may be introduced into a host cell by any method known to one of skill in the art and the nucleic acid constructs may be carried extrachromosomally within a host cell or may be integrated into a host cell chromosome, as desired. A vector for use in a prokaryote host, such as a bacterial cell, includes a replication system allowing it to be maintained in the host for expression or for cloning and amplification. A vector may be present in the cell in either high or low copy number. Generally, about 5 to about 200, and usually about 10 to about 150 copies of a high copy number vector are present within a host cell. A host cell containing a high copy number vector will preferably contain at least about 10, and more preferably at least about 20 plasmid vectors. Generally, about 1 to 10, and usually about 1 to 4 copies of a low copy number vector will be present in a host cell.

In many aspects, bacteria are used as host cells. Examples of bacteria include, but are not limited to, Gram-negative and Gram-positive organisms. In one aspect an *E. coli* expression system suitable for T7 protein expression may be used. Examples of T7 expression strains can include, without limitation, BL21(DE3), BL21(DE3)pLysS, BLR(DE3) pLysS, Tuner(DE3)pLysS, Tuner(DE3), Lemo21(DE3), NiCO2(DE3), Oragami2(DE3), Origami B(DE3), Shuffle T7 Expres, HMS174(DE3), HMS174(DE3)pLysS, DH5aplhaE, Rosetta2(DE3), Rosetta2(DE3)pLysS, NovaBlue(DE3), Rosetta-gami B, Rosetta-gami B(DE3), Rosetta-gami B(DE3)pLysS, Rosetta Blue (DE3), Novagen(DE3), Novagen(DE3)pLysS.

An expression vector may be introduced into bacterial cells by commonly used transformation/infection procedures. A nucleic acid construct containing an expression cassette can be integrated into the genome of a bacterial host cell through use of an integrating vector. Integrating vectors usually contain at least one sequence that is homologous to the bacterial chromosome that allows the vector to integrate. Integrating vectors may also contain bacteriophage or transposon sequences. Extrachromosomal and integrating vectors may contain selectable markers to allow for the selection of bacterial strains that have been transformed.

Useful vectors for an *E. coli* expression system may contain constitutive or inducible promoters to direct expression of either fusion or non-fusion proteins. With fusion vectors, a number of amino acids are usually added to the expressed target gene sequence. Additionally, a proteolytic cleavage site may be introduced at a site between the target recombinant protein and the fusion sequence. Once the fusion protein has been purified, the cleavage site allows the target recombinant protein to be separated from the fusion sequence. Enzymes suitable for use in cleaving the proteolytic cleavage site include TEV, Factor Xa and thrombin. Fusion expression vectors which may be useful in the present can include those which express, for example and without limitation, Maltose Binding Protein (MBP), Thioredoxin (THX), Chitin Binding Domain (CBD), Hexahistadine tag (His-tag), glutathione-S-transferase protein (GST), FLAG peptide, N-utilization substance (NusA), or Small ubiquitin modified (SUMO) fused to the target recombinant enzyme.

Methods for introducing exogenous DNA into a host cell are available in the art, and can include the transformation of bacteria treated with $CaCl_2$ or other agents, such as divalent cations and DMSO. DNA can also be introduced into host cells by electroporation, use of a bacteriophage, ballistic transformation, calcium phosphate co-precipitation, spheroplast fusion, electroporation, treatment of the host cells with lithium acetate or by electroporation. Transformation procedures usually vary with the bacterial species to be transformed.

Following transformation or transfection of a nucleic acid into a cell, the cell may be selected for the presence of the nucleic acid through use of a selectable marker. A selectable marker is generally encoded on the nucleic acid being introduced into the recipient cell. However, co-transfection of a selectable marker can also be used during introduction of nucleic acid into a host cell. Selectable markers that can be expressed in the recipient host cell may include, but are not limited to, genes that render the recipient host cell resistant to drugs such as actinomycin Cl, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. Selectable markers may also include biosynthetic genes, such as those in the histidine, tryptophan, and leucine biosynthetic pathways. Upon transfection or transformation of a host cell, the cell is placed into contact with an appropriate selection agent.

In one aspect, a depolymerization component of a process can utilize a combination of different microorganisms and/or enzymes, including combinations of transformed and natural microorganisms and/or modified and natural enzymes. For example, in one aspect, a depolymerization component of a process can include one or more microorganisms that naturally secrete depolymerase enzyme combined with one or more microorganisms that have been genetically modified in order to secrete depolymerase enzyme. A genetically modified microorganism, for instance, can be used to fine tune a system based on environmental conditions and feed supply, among other characteristics.

By way of example, one or more natural and/or transformed microorganisms and/or their respective enzymes may be used based upon one or more of the following factors: easy and fast to grow in high density, do not require special media, aerobic, kinetically fast, stable, tolerant to an extreme environment (e.g., high salt environment, extreme temperature environment, etc.), able to produce readily purifiable enzymes, lack an unusual isoelectric point, do not require heightened biosafety measures, do not comprise cysteine residues in excess, overall non-esoteric, and available for purchase commercially. For instance, the present disclosure has found that by limiting the amount of cysteine residues, improved folding may be achieved. Selection based upon one or more of the above factors can further improve the speed and efficiency of the depolymerization component, allowing improved throughput of the industrial process.

Metabolic Polymer Production

According to disclosed methods, HA monomer released upon depolymerization of PHA contained in a post-consumer product (herein referred to as post-consumer HA monomer) can be contacted with a microorganism capable of producing PHA. The contact can take place under conditions that encourage metabolism of the HA monomer by the organism as a carbon source and subsequent metabolic production of PHA by the microorganism. The PHA thus produced can be suitable for use in formation of new consumer products. Thus, a circular and sustainable polymer system can be created.

Conditions of the culture can be controlled to encourage HA metabolism and PHA production by the organism. Such conditions can include nutrient source deprivation optionally in conjunction with other environmental conditions that can stress the microorganism and encourage PHA production as an energy sink.

In one embodiment culturing conditions can include limiting carbon sources to the microorganism. For instance, post-consumer HA can be provided to the organism as the only metabolic carbon source. In some embodiments, other carbon sources may be included in the culture, but may be present in limited amounts, for instance in micromolar concentrations. For instance, any metabolic carbon source (e.g., sugars, organic acids, etc. or combinations thereof) present in a culture other than post-consumer HA monomer can be present in a concentration of about 2 mM or less, such as about 1 mM or less, such as about 500 µM or less.

Stressful culturing conditions that can encourage HA metabolism and PHA production by a microorganism can include deprivation of other nutrients, e.g., nitrogen and/or phosphate-containing nutrients so as to encourage formation of PHA as an energy sink for the organism. In one embodiment, culturing conditions can include deprivation of phosphate-containing nutrients, so as to prevent formation of polyphosphate by the microorganism, which is another common metabolic process utilized by microorganisms as an energy sink in times of stress. Deprivation of a nutrient source can include complete absence of the nutrient source in the culture or presence of the nutrient source in amounts so as to stress the metabolic processes of the microorganism, e.g., about 50% or less of the concentration of the nutrient present in a non-stressed culture environment.

Stressful culturing conditions can include environmental conditions, optionally in conjunction with stressful nutrient conditions. For instance, a culture can be carried out near the limits of pressure, temperature, salinity, pH, etc. within which the microorganism normally functions. By way of example, a mesophilic organism can be cultured at temperature conditions of from about 15° C. to about 25° C. or from about 40° C. to about 50° C. (near an end of the normal culture range), at saline conditions of from about 0.5 parts per thousand (ppt) to about 8 ppt or from about 15 ppt to about 22 ppt, at pH conditions of from about pH 4 to about pH 6 or from about pH 9 to about pH 10, at pressure conditions of from about 10 kPa to about 30 kPa or from about 100 kPa to about 120 kPa, or any combination thereof.

Microorganisms for use in the PHA production component of a process can be selected and/or modified to overcome issues or deficiencies so as to form PHA by use of a metabolic process using HA as a carbon source. Particularly, microorganisms can be selected based on factors such as those mentioned above with regard to microorganisms for use in a depolymerization component of a process. Such factors can include, but are not limited to, easy and fast to grow in high density, do not require special media, aerobic, kinetically fast, stable, tolerant to an extreme environment (e.g., high salt environment, extreme temperature environment, etc.), able to produce readily purifiable enzymes, lack an unusual isoelectric point, do not require heightened biosafety measures, do not comprise cysteine residues in excess, overall non-esoteric, available for purchase commercially, or a combination thereof.

In some aspects, a microorganism for metabolic production of PHA using post-consumer PA monomer can also produce a PHADase as may be utilized (either as-produced or purified) or modified for use in the depolymerization component of a process. Species from the genus *Lysobacter* can be utilized in one embodiment, as they can produce PHADase capable of active hydrolyzing PHB and also contain the biochemical machinery to metabolize HB and to internally form PHB. *Lysobacter* species are naturally found in soil, and by use of such a species, one embodiment of a process can be conducted as part of a compostable process rather than requiring formation and processing of a liquid culture in a bioreactor or series of bioreactors.

Exemplary *Lysobacter* species that produce both a PHA polymerase and a depolymerase as may be utilized in a process can include, without limitation, those provided in Table 1, below:

TABLE 1

| Organism | Accession Number | |
|---|---|---|
| | Polymerase | Depolymerase |
| *Lysobacter aestuarii* | WP_141519092 | QDH70273 |
| *Lysobacter antibioticus* | WP_057917797 | WP_075575206 |
| *Lysobacter antibioticus* | WP_064749485 | WP_057971776 |
| *Lysobacter antibioticus* | WP_031370714 | WP_057970457 |
| *Lysobacter bugurensis* | WP_189454736 | WP_189453172 |
| *Lysobacter capsici* | WP_036103061 | WP_036102479 |
| *Lysobacter capsici* | WP_191821024 | WP_082723829 |
| *Lysobacter enzymogenes* | WP_057947866 | WP_074867011 |
| *Lysobacter enzymogenes* | WP_206409599 | WP_206412663 |
| *Lysobacter enzymogenes* | WP_123648422 | WP_096378935 |
| *Lysobacter enzymogenes* | WP_078996336 | WP_096378891 |
| *Lysobacter lacus* | WP_149351326 | WP_149353094 |
| *Lysobacter lycopersici* | WP_143878270 | WP_111268077 |
| *Lysobacter maris* | WP_111268029 | WP_141481346 |
| *Lysobacter niastensis* | WP_194931164 | WP_194930566 |
| *Lysobacter profundi* | WP_159015985 | WP_199268782 |
| *Lysobacter* sp. | MBA2238340 | MBA3486130 |
| *Lysobacter* sp. | NOT90012 | NOT88901 |
| *Lysobacter* sp. | TXI44079 | TXI49260 |
| *Lysobacter* sp. | TBR06965 | TBR07230 |
| *Lysobacter* sp.A03 | WP_043958955 | WP_043958589 |
| *Lysobacter* sp.cf310 | WP_091637072 | SFK67843 |
| *Lysobacter* sp.H21R20 | WP_193987019 | WP_193986963 |
| *Lysobacter* sp.H21R4 | WP_194342245 | WP_194342197 |
| *Lysobacter* sp.H23M41 | WP_194035564 | WP_194035504 |
| *Lysobacter* sp.R19 | WP_200614426 | MBK3415203 |
| *Lysobacter* sp.Root604 | WP_056175356 | WP_056174125 |
| *Lysobacter* sp.Root690 | WP_056115057 | WP_056115653 |
| *Lysobacter* sp.Root916 | WP_057163275 | WP_082578417 |
| *Lysobacter* sp.Root983 | WP_057159495 | WP_057162992 |
| *Lysobacter* sp.TY2-98 | WP_115646306 | WP_057159102 |
| *Lysobacter spongiae* | WP_182687030 | WP_182685163 |
| *Lysobacter spongiicola* | WP_078757079 | WP_200809237 |

Of course, species for use in metabolic formation of new PHA from post-consumer HA monomer are not limited to those that also produce a PHADase, and a PHA-producing microorganism can be utilized in conjunction with one or more other microorganiem and/or PHADase that differ from one another as discussed previously. Exemplary *Lysobacter* species that are only documented as producing a PHA polymerase as may be utilized in a process can include, without limitation, those provided in Table 2, below:

TABLE 2

| Organism | Polymerase Accession Number |
|---|---|
| *Lysobacter* | WP_036193982 |
| *Lysobacter alkalisoli* | WP_141625093 |
| *Lysobacter arseniciresistens* | WP_036208009 |
| *Lysobacter daejeonensis* | WP_036135021 |
| *Lysobacter dokdonensis* | WP_036108095 |
| *Lysobacter enzymogenes* | WP_207524961 |
| *Lysobacter enzymogenes* | WP_096377760 |
| *Lysobacter enzymogenes* | WP_074869551 |
| *Lysobacter gilvus* | WP_156641946 |
| *Lysobacter gummosus* | WP_057943197 |
| *Lysobacter maris* | WP_141483002 |
| *Lysobacter oculi* | WP_112926105 |
| *Lysobacter panacisoli* | WP_200604936 |
| *Lysobacter penaei* | WP_182668477 |
| *Lysobacter prati* | WP_158731614 |
| *Lysobacter psychrotolerans* | WP_123087040 |
| *Lysobacter pythonis* | WP_122100479 |
| *Lysobacter ruishenii* | WP_144812683 |

TABLE 2-continued

| Organism | Polymerase Accession Number |
|---|---|
| *Lysobacter segetis* | WP_133478701 |
| *Lysobacter silvestris* | WP_103075695 |
| *Lysobacter silvisoli* | WP_115858207 |
| *Lysobacter soli* | WP_157029884 |
| *Lysobacter* sp. | NUO78313 |
| *Lysobacter* sp. 17J7-1 | WP_133500014 |
| *Lysobacter* sp. Alg18-2.2 | WP_147890376 |
| *Lysobacter* sp. Cm-3-T8 | WP_206859118 |
| *Lysobacter* sp. H23M47 | WP_194037433 |
| *Lysobacter* sp. HDW10 | WP_166296513 |
| *Lysobacter* sp. II4 | WP_187713470 |
| *Lysobacter* sp. N42 | WP_132328958 |
| *Lysobacter* sp. OAE881 | WP_192630396 |
| *Lysobacter* sp. Root494 | WP_056131727 |
| *Lysobacter* sp. URHA0019 | WP_027083001 |
| *Lysobacter* sp. WF-2 | WP_117202823 |
| *Lysobacter* sp. yr284 | WP_091793341 |
| *Lysobacter tabacisoli* | WP 119719022 |
| *Lysobacter telluris* | WP 166211016 |
| *Lysobacter tolerans* | WP 076587639 |
| *Lysobacter tolerans* | SIP87483 |
| *Lysobacter xinjiangensis* | WP_189447436 |
| unclassified *Lysobacter* | WP_055899693 |

Other organiems can be utilized, in conjunction with those of the genus Lysobacter or instead of such. By way of example, and without limitation, Table 3 presents examples of other species and ascension numbers for their PHA polymerase as may be utilized that can be encouraged to metabolize HA monomer as a carbon source in production of new PHA.

TABLE 3

| Organism | Ascension No. |
|---|---|
| *Aliivibrio finisterrensis* | WP_151654375 |
| *Aliivibrio fischeri* | WP_065624776 |
| *Aliivibrio sifiae* | WP_105055326 |
| *Aliivibrio* sp | MBL4831209 |
| *Aliivibrio* sp. 1S128 | WP_065600195 |
| *Aliivibrio* sp. EL58 | WP_122034402 |
| *Aliivibrio* sp. SR45-2 | WP_182699437 |
| *Caballeronia arvi* | WP_061150199 |
| *Caballeronia calidae* | WP_062608567 |
| *Caballeronia hypogeia* | WP_061169280 |
| *Caballeronia insecticola* | BAN58336 |
| *Caballeronia pedi* | WP_061178553 |
| *Caballeronia terrestris* | WP_087660849 |
| *Dokdonella koreensis* | WP_067647850 |
| *Dyella caseinilytica* | WP_188798656 |
| *Dyella choica* | WP_126682794 |
| *Dyella dinghuensis* | WP_126672795 |
| *Dyella flava* | WP_204681682 |
| *Dyella jiangningensis* | AHX12796 |
| *Dyella kyungheensis* | WP_204634561 |
| *Dyella mobilis* | WP_204632428 |
| *Dyella monticola* | WP_115496150 |
| *Dyella nitratireducens* | WP_188792429 |
| *Dyella psychrodurans* | RDS86489 |
| *Dyella soli* | WP_131407398 |
| *Dyella solisilvae* | WP_114823339 |
| *Dyella* sp. 7MK23 | WP_192556083 |
| *Dyella* sp. ASV21 | WP_199100073 |
| *Dyella* sp. ASV24 | WP_199038667 |
| *Dyella* sp. C11v | WP_157956602 |
| *Dyella* sp. C9 | WP_114241222 |
| *Dyella* sp. DHC06 | WP_130620551 |
| *Dyella* sp. EPa41 | WP_201314821 |
| *Dyella* sp. G9 | WP_187056353 |
| *Dyella* sp. M7H15-1 | WP_164931796 |
| *Dyella* sp. M7H15-1 | QAU23859 |
| *Dyella* sp. OK004 | WP_090451505 |
| *Dyella* sp. S184 | WP_158755276 |
| *Dyella* sp. SG562 | WP_167257616 |

TABLE 3-continued

| Organism | Ascension No. |
|---|---|
| Dyella sp. SG609 | WP_168647555 |
| Dyella sp. YR388 | WP_147455377 |
| Dyella tabacisoli | WP_114845894 |
| Fluoribacter bozemanae | WP_058459414 |
| Fluoribacter dumoffii NY 23 | KTC90057 |
| Fluoribacter gormanii | KTD05403 |
| Microscilla marina | WP_002702565 |
| Pseudomonas aeruginosa | AHJ25666 |
| Pseudomonas thermotolerans | WP_027896668 |
| Pseudomonas mediterranea | WP_047699726 |
| Psychrobacter sp. | QCF41916 |
| Psychromonas sp. MB-3u-54 | WP_101038601 |
| Psychromonas sp. psych-6C06 | WP_101107093 |
| Psychromonas sp. RZ22 | WP_134276148 |
| Psychromonas sp. Urea-02u-13 | WP_101081048 |
| Rhodanobacter denitrificans | NMW25143 |
| Rhodanobacter fulvus | WP_040670830 |
| Rhodanobacter glycinis | WP_140650985 |
| Xanthomonas sp. NCPPB 1128 | WP_048489717 |
| Xanthomonas vasicola | WP_039434864 |
| Rhodanobacter lindaniclasticus | WP_136257156 |
| Rhodanobacter panaciterrae | WP_189440331 |
| Rhodanobacter sp. 7MK24 | WP_192155134 |
| Rhodanobacter sp. A1T4 | WP_184673302 |
| Rhodanobacter sp. B04 | WP_077555812 |
| Rhodanobacter sp. B05 | WP_077513483 |
| Rhodanobacter sp. C01 | WP_077442012 |
| Rhodanobacter sp. C03 | WP_077518181 |
| Rhodanobacter sp. C05 | WP_077443954 |
| Rhodanobacter sp. C06 | WP_077485236 |
| Rhodanobacter sp. DHB23 | WP_192106892 |
| Rhodanobacter sp. DHG33 | WP_192163461 |
| Rhodanobacter sp. L36 | WP_158885070 |
| Rhodanobacter sp. MP1X3 | WP_184604847 |
| Rhodanobacter sp. OK091 | WP_072760944 |
| Rhodanobacter sp. OR444 | WP_027492196 |
| Rhodanobacter sp. PCA2 | WP_181302403 |
| Rhodanobacter sp. Root480 | WP_056080179 |
| Rhodanobacter sp. Root627 | WP_082545971 |
| Rhodanobacter sp. Root627 | KRA35976 |
| Rhodanobacter sp. SCN 67-45 | ODT97084 |
| Rhodanobacter sp. SCN 68-63 | ODV10878 |
| Rhodanobacter sp. Soil772 | WP_056386006 |
| Rhodanobacter sp. T12-5 | WP_149365305 |
| Rhodanobacter sp. TND4EH1 | WP_099652471 |
| Rhodanobacter sp. TND4FH1 | WP_133950922 |
| Rhodanobacter spathiphylli | WP_007805234 |
| Rhodanobacter thiooxydans | WP_008435591 |
| Stenotrophomonas chelatiphaga | WP_057508611 |
| Stenotrophomonas maltophilia | WP_019338202 |
| Stenotrophomonas panacihumi | WP_057643119 |
| Stenotrophomonas pavanii | WP_057494653 |
| Stenotrophomonas rhizophila | WP_038687867 |
| Stenotrophomonas sp. DDT-1 | WP_061479060 |
| Stenotrophomonas sp. RIT309 | WP_032976188 |
| Stenotrophomonas sp. SKA14 | WP_008265690 |
| Vibrio aestuarianus | WP_168520800 |
| Vibrio antiquarius | WP_074190087 |
| Vibrio aquaticus | WP_126574305 |
| Vibrio tasmaniensis | WP_102248967 |
| Xanthomonadales bacterium | OZB58863 |
| Xanthomonas albilineans | WP_012916138 |
| Xanthomonas arboricola | WP_039511932 |
| Xanthomonas axonopodis | WP_042822558 |
| Xanthomonas bromi | PPV05022 |
| Xanthomonas campestris | WP_011037305 |
| Xanthomonas cannabis | WP_047694901 |
| Xanthomonas citri | WP_046832369 |
| Xanthomonas euvesicatoria | WP_136732577 |
| Xanthomonas fragariae | WP_002802267 |
| Xanthomonas hortorum | WP_006450930 |
| Xanthomonas hyacinthi | WP_046978386 |
| Xanthomonas oryzae | WP_014503544 |
| Xanthomonas phaseoli | WP_017157553 |
| Xanthomonas pisi | WP_046964104 |
| Xanthomonas sacchari | WP_043092075 |
| Xanthomonas sp. Leaf131 | WP_055826366 |
| Xanthomonas translucens | WP_003466505 |
| Xanthomonas vesicatoria | WP_039424128 |

In some embodiments, the selection of the microorganisms of the PHA production component can be chosen to match the needs of the depolymerization process. For instance, if there is a need/desire to run both components of a process simultaneously or separately, but at the same elevated temperature then the enzyme(s) and/or microorganisms can be thermophiles that function in the same temperature range. Similarly, if there is a need or desire to run both components of a process in the presence of high salt, then the enzyme(s) and/or microorganisms for use can be halophiles. Similarly, if less extreme conditions are desired for the decontamination and depolymerization process, for instance due to the known contaminants, and it is desired to run the metabolic production component at the same conditions, then extremophilic enzyme(s) and/or microorganisms can be used for both components that exhibit high activity in those less extreme conditions.

Alternatively, in those embodiments in which the two components of a process are carried out separately from one another, i.e., at different times and/or different locations, the selection of microorganisms for the metabolic PHA production component can be selected based upon desired production parameters, e.g., kinetics, efficiency, etc. In such an embodiment, the two components of a process can be carried out at the same or different conditions, and when carried out at different conditions, the conditions can differ by one or more environmental conditions including, without limitation, temperature, salt content, pressure, acid/alkali content, radiation, etc.

Bioreactor System

Figure 5:
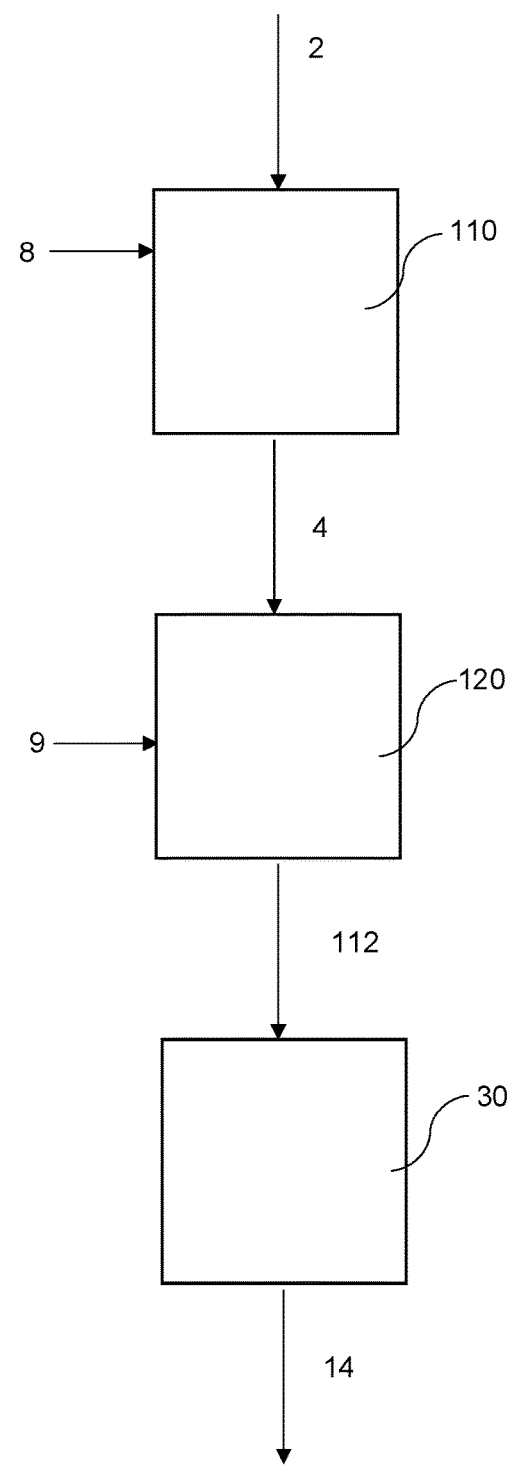
FIG. 5 schematically illustrates another embodiment of a bioreactor system as may be utilized in carrying out a process as disclosed herein.

A bioreactor system can be utilized for carrying out disclosed methods. A bioreactor system can include a single reaction vessel or multiple reaction vessels as may be utilized in carrying out a depolymerization component and a metabolic production component as discussed herein. By way of example, FIG. 4 illustrates a bioreactor system including a single vessel 10 within which both a depolymerization of a PHA-containing feed 2 and polymer can be carried out. FIG. 5 illustrates another bioreactor system including a first vessel 110 within which depolymerization of a PHA feed can be carried out and a second vessel 120 within which a microorganism can be cultured in conjunction with HA monomer 4 obtained from the first vessel 110 to produce new PHA. Moreover, a single vessel 10 can be composed of two or more internal compartments that are connected in a closed manner, so as to separate components of an overall process and allow for separation operations (e.g., filtration), modification of environmental factors, modification of processing aids, etc., between components of the overall process.

In either a single or multiple vessel embodiments, a process can be controlled either manually or automatically. For instance a process can be carried out according to a continuous, semi-batch, batch process, or perfusion mode with any combination of automatic and manual control mechanisms.

By way of example the PHA-containing feed 2 can contains discarded incontinence products or other polymer based post-consumer product that includes one or more PHA. Incontinence products include, for example, diapers, training pants, swim pants, adult incontinence products, feminine hygiene products, and the like. These products typically include a water permeable liner, an outer cover, and an absorbent structure positioned between the liquid permeable liner and the outer cover. The incontinence products may contain biopolymers in amounts greater than about 5% by weight, such as in amounts greater than about 10% by weight, such as in amounts greater than about 20% by weight, such as in amounts greater than about 30% by weight, such as in amounts greater than about 40% by weight, such as in amounts greater than about 50% by weight, such as in amounts greater than about 60% by weight, such as in amounts greater than about 70% by weight.

PHA-containing feed 2 can be provided to a vessel 10/110, in any suitable form. For instance, PHA-containing feed can include the polymer in its original consumer form, or a post-consumer product may be pre-treated, e.g., may be chopped or crushed, prior to addition of the feed to a vessel 10/110. For instance, as discussed above, in some embodiments, little or no pre-cleaning or sanitizing step is performed prior to addition of the PHA-containing feed 2 to a vessel 10/110, for instance in those embodiments in which one or both components of a process are carried out in an extreme environment in which contaminants may be degraded or otherwise rendered non-hazardous.

As shown in FIG. 4 and FIG. 5, feed 2 including one or more post-consumer PHA polymers can be fed into vessel 10/110 within which PHA of the feed can be depolymerized by the action of one or more suitable PHADase. A PHADase 8 can be supplied to the vessel 10/110 as a purified PHADase in an enzyme-based depolymerization.

Alternatively, a depolymerization component can be a bacteria-based process, in which case a PHADase can be expressed within a vessel 10 from a suitable microorganism culture, which can optionally be fed to a vessel 10 prior to, concurrent with, or following introduction of feed 2 into the vessel 10. As discussed previously, combinations of PHADase sources are also encompassed herein, including combinations of natural and/or modified purified PHADase which can optionally be combined with one or more PHADase-expressing microorganisms, and such microorganisms can likewise express any combination of natural and modified PHADase.

Additional materials as would be known in the art can be combined with the feed 2 and the PHADase of the depolymerization component. For instance, suitable growth media may be necessary if a bacteria-based depolymerization component is utilized. Likewise, in those embodiments in which a depolymerization component is carried out in an extreme environment, suitable materials, e.g., salts, acids, bases, etc., can be fed to a vessel 10/110.

Conditions within a vessel 10/110 can be controlled as necessary to encourage depolymerization of a PHA polymer. For instance, a vessel 10/110 can include an agitator that may be run continuously through a depolymerization component or may be started and stopped intermittently as known in the art.

In a single vessel system as illustrated in FIG. 4, a depolymerization component and a PHA formation component can be carried out concurrently or separately. For instance, in one embodiment a PHA depolymerase reaction can be allowed to proceed until all or a portion of the PHA has been depolymerized following which the HA monomer can be utilized as a carbon source in microorganism metabolic production of PHA polymer. For instance, and as will be discussed in greater detail in regard to the examples below, the reaction may be allowed to proceed until a decrease in PHA depolymerase is observed, for instance according to visual observance of a system, fluorescence emission of a system, or according to passing of a predetermined reaction time period. In one aspect, the completion of the depolymerization component of a process may be determined through determination of a plateau in enzyme activity. Alternatively, one or more optical or visual measurements may be taken. For instance, PHB is insoluble in most solvents creating a high optical density at 600 nm, where HB is generally soluble due to its smaller molecular weight. Therefore, a decreased optical density, such as identification of an optical density density of about 0.9 or less, such as about 0.8 or less, such as about 0.7 or less, such as bout 0.6 or less, such as about 0.5 or less, such as about 0.4 or less, such as about 0.3 or less, such as about 0.2 or less, such as about 0.1 or less, as measured at 600 nm, can be utilized to determine that PHB of a feed 2 has been depolymerized to provide HB monomer.

Upon determination of completion of a depolymerization component of a process, a microorganism 9 can be fed to the vessel in conjunction with any additional components necessary for culturing and in conjunction with any variation in the vessel environment necessary for culturing. The HA monomer produced earlier can then be available as carbon-source for the microorganism culture.

In one aspect, microorganisms for use in either component of a process can be encapsulated in a carrier, such as a polymer carrier. A polymer carrier can be a material that is highly water absorbent without being water soluble. In one aspect, for instance, a polymer carrier is in the form of a gel when combined with water, can be dehydrated and converted into the form of a solid, and then capable of being rehydratable when contacted with moisture. In this manner, the one or more microorganisms can be combined with the polymer carrier in the form of a gel. Once blended together, water can then be removed in order to form a solid. The solid can be formed into any suitable shape and contacted with post-consumer product 104 waste materials. In order to degrade polymers contained in the waste material, the solid material is contacted with moisture that causes the carrier polymer to rehydrate. Once rehydrated, the microorganisms can be released from the polymer gel or can secrete enzymes that are released from the polymer gel.

A single vessel system as illustrated in FIG. 4 may in one embodiment be utilized to carry out both components of a process simultaneously. For instance a single microorganism that expresses a PHADase and is also capable of metabolizing the HA monomer thus released as a carbon source to produce new PHA can be cultured within the single reaction vessel 10 in conjunction with a feed 2. As discussed previously, such a microorganism may be utilized alone or in conjunction with additional enzyme and/or cocultured with additional microorganism to fine tune a system.

A process can be allowed to proceed until the HA carbon source is exhausted and microorganism growth and PHA production ceases, upon which microorganism can be removed 12 from the vessel 10 and post-processing 30 carried out including, e.g., polymer extraction, polymer purification, waste removal, etc. to produce a PHA product 14 suitable for use in formation of new product. Determination of completion of a production batch can be determined according to standard procedure, such as those discussed above and in the example section below to determine a plateau in growth and/or a depletion of carbon source in the culture media. In some embodiments, a continuous system can be utilized in which microorganisms are removed from a vessel 12 continuously or in a semi-batch approach and subjected to post-processing for extraction of new polymer.

FIG. 5 illustrates a two vessel system in which a first depolymerization component of a process is carried out in a first vessel 110 and following depolymerization of PHA of a feed 2 by use of one or more purified PHADase 8 fed to the vessel 10, PHADase expressed by one or more microorganisms cultured within the vessel 10 in conjunction with the feed, or any combination thereof, HA monomer thus formed can be removed from the first vessel 10 and provided 4 to a second vessel 120, where it can be metabolized by microorganism 9 cultured within the second vessel 120.

In such an embodiment, HA monomer stream 4 can be subjected to processing prior to utilization as a carbon source by the microorganisms 9 of the second vessel 120 in a metabolic process. For instance, HA monomer can be separated from other components of a stream 4 by filtration. In one aspect, HA monomer can be separated by use of a size exclusion filter (such as a molecular weight cutoff filter), having a size of about 30 kD or less, such as about 25 kD or less, such as about 20 kD or less, such as about 15 kD or less, such as about 10 kD or less, such as about 5 kD or less, such as about 4.5 kD or less, such as about 4 kD or less, such as about 3.5 kD or less, such as about 3 kD or less, such as about 2 kD or greater, such as about 3 kD or greater, or any ranges or values therebetween.

For instance, a filter may be sized appropriately to retain any remaining pieces of the post-consumer product and any remaining PHA, as well as any remaining PHADase. Retention of PHADase can be useful, as this can prevent depolymerization of PHA produced in the second vessel 120. Moreover, removal of larger waste particles prior to formation of new polymer can be utilized to control the environment within the second vessel 120.

In one embodiment, stream 4 from a depolymerization component can be subjected to an ion exchange filter (such as a Dowex ion exchange bed). This may be particularly beneficial when the enzyme utilized in the depolymerization component differs with regard to preferred environment as compared to the microorganism utilized to metabolically produce new polymer. By way of example, in those embodiments in which a halophilic enzyme is used in a depolymerization component (e.g. when the environment within the first vessel 110 includes a high salt concentration). Treatment of the stream 4 by use of an ion exchange filter can remove salt from the stream 4 and provide a salt free HA monomer to the second vessel 120.

Similar to a single vessel system a two vessel system can allow the microorganism culture to grow until the HA carbon source is exhausted and microorganism growth and PHA production ceases, upon which microorganism can be removed 112 from the vessel 120 and post-processing 30 carried out including, e.g., polymer extraction, polymer purification, waste removal, etc. to produce a PHA product 14 suitable for use in formation of new product.

The present disclosure may be better understood with reference to the following examples.

Example 1

Chemicals

All general chemicals, media components, and granulated PHB were obtained from Millipore-Sigma, Inc. Molecular biology reagents including competent cells, PCR reagents, and all protein purification reagents were purchased from New England Biolabs, Inc.

Bacterial Growth

*Lysobacter enzymogenes* (ATCC 55439) was grown in Trypticase Soy Broth (per liter: 17.0 g tryptone, 3.0 g soytone, 2.5 g dextrose, 5.0 g NaCl, 2.5 g $K_2HPO_4$; pH 7.3) at 30° C. Overnight cultures were harvested by centrifugation at 10,000× g for 15 minutes, resuspended in phosphate buffered saline (PBS) and recentrifuged to remove all media components. This was performed twice. The final bacterial pellet was resuspended to a final concentration of $1.0 \times 10^8$ cfu/mL in PBS prior to use. For PHB depolymerization or polymerization reactions, washed cells were transferred to flasks containing M9 media supplemented with 1× MEM amino acids, 1.0 mM glutamine, 1×M9 salts, 1× MEM vitamins, and 10% (w/v) hydroxybutyrate. Growth occurred at 30° C.

PHB Depolymerase Expression Construct

The amino acid sequence of the *L. enzymogenes* PHB depolymerase (WP_074867011) was utilized as a source of overexpressed recombinant protein. The recombinant *L. enzymogenes* PHBDase is comprised of 570 amino acids and is 59.1 kDa in mass (including the N-ter glycine). The enzyme has a pI of 4.75 and contains eight cysteine residues. The sequence of the protein is provided in FIG. 1 (SEQ ID NO: 1). The 11 tryptophan residues impart significant fluorescent signal which is useful for stability and unfolding studies. The protein purification was straightforward using a T7 expression system and homogeneous enzyme was produced at a yield of 23.4 mg/L.

The first 35 amino acids (MSAVRSLHRSAP-RAARWLSLSVLLAGVCCAAPAFA-SEQ ID NO: 2) constituted a signal sequence and this sequence was removed from the construct. A histidine expression sequence and a TEV protease cleavage signal sequence: MHHHHHHGSENLYFQG (SEQ ID NO: 3) were appended to the amino terminal portion of the enzyme sequence. Upon cleavage the recombinant proteins had an N-ter sequence that began with a glycine residue. This new amino acid sequence was reverse translated to DNA and codon optimized for expression in *E. coli* using the program Gene Designer from ATUM, Inc. The gene was assembled using standard PCR techniques by ATUM, Inc. and cloned into the expression vector p454-MR (amp$^r$, medium strength ribosomal binding site). The insert was verified by DNA sequencing after construction.

Expression and Purification of PHB Depolymerase

The expression plasmid was used to transform chemically competent Oragami2-(DE3) bacteria. Single colonies were selected from LB-Amp plates and used for expression screening. Colonies were grown at 37° C. for 12 hours in LB media supplemented with 100 µg/mL ampicillin. This culture was used to inoculate fresh LB-AMP flasks at a 1:100 inoculum. These cultures were grown at 37° C. until $OD^{595}=0.4$ (typically 4 hours) at which time Isopropyl β-D-1-thiogalactopyranoside (IPTG) was added to a final concentration of 1 mM. Growth was continued for 12 hours. Cells were harvested by centrifugation at 10,000× g for 15 minutes and frozen at −80° C. until use (minimal time frozen was 24 hours). Cells were thawed on ice and were resuspended in Buffer A (0.5 M NaCl, 20 mM Tris-HCl, 5 mM imidazole, pH 7.9) (typically 1 mL per gram of cells). Cells were disrupted via two passes through a French Press followed by centrifugation at 30,000× g for 30 minutes. The crude extract was mixed with an equal volume of charged His-Bind resin slurry and the mixture was poured into 5 cm×4.9 cc column. The column was washed with 10 column volumes of wash buffer (0.5 M NaCl, 20 mM Tris-HCl, 60 mM imidazole, pH 7.9) at a flow rate of 0.2 mL/min. Enzyme was eluted from the column with the addition of 3 column volumes of 0.5 M NaCl, 20 mM Tris-HCl, 1.0 M imidazole, pH 7.9. Fractions were collected (1.0 mL). Fractions containing enzyme were pooled after analysis by SDS PAGE. The pooled fractions were applied to a 70 cm×4.9 cc Sephadex G-75 column (10 mM Tris-HCl, pH 7.5, 1 mM EDTA). Fractions containing homogeneous protein were pooled (after inspection by SDS PAGE), concentrated to 5 mg/ml via Centricon filters. Enzyme was stored frozen at −20° C. until use. The histidine tag region was removed from the enzymes using TEV protease. Protein was diluted to 1.0 mg/ml into 10 mM Tris-HCl, PH 7.5, 25 mM NaCl. 100 U of TEV protease was added per mg of enzyme (approximate ratio of 1:100 (w/w). The reaction was allowed to proceed for 16 h at 4° C. The mixture was passed over a charged nickel column. One column volume of eluent was collected representing purified tag-free enzyme.

PHB Depolymerase Assay

An assay was utilized to measure β-hydroxybutyrate directly using the Sigma-Aldrich hydroxybutyrate assay kit MAK272. HB was measured fluorometrically ($\lambda_{ex}$=535 nm, λem=587 nm). Aliquots (10 µL) were removed from the PHB depolymerase reaction at various time points, mixed with 50 µL of the supplied HB assay buffer, and pipeted into a well of a black, flat bottomed, 96-well plate. The plate was incubated at room temperature in the dark for 30 minutes. Fluorescence emission intensity was measured using a Molecular Dynamics SpectraMax M5. Fluorescence readings were converted to HB concentration via comparison to a standard curve constructed from known concentrations of pure hydroxybutyrate. All kinetic parameters are calculated per Segel (1993).

PHB Film Formation

PHB films were formed via solvent casting from heated chloroform as described by (Anbukarasu and Sauvageau, 2015). PHB granules were mixed with chloroform to a final concentration of 50 mg/mL and the mixture was heated to 70° C. (covered) with stirring for one hour (the time to fully dissolve the PHB granules). The solution was poured into glass petri dishes to a depth of approximately 2 mm and the solvent was allowed to evaporate at 25° C. The samples were aged for five days (1.0 atm, 25° C.) and then were vacuum dried for 3 hours to remove any remaining chloroform. Final films were removed from the petri dish and cut into 2 cm×2 cm squares.

PHB Extraction From Bacterial Cells

PHB was extracted from cells using a modified procedure (Mostafa et al., 2020). Bacterial pellets were dried at 70° C. for two hours and the dried cells were washed with acetone and ethanol for 20 minutes and treated with 50 mL of 30% sodium hypochlorite and 50 mL of chloroform. This mixture was incubated for 1 h at 37° C. in a shaker at 150 rpm and then centrifuged at 10,000× g for 45 minutes. The supernatant was decanted, and the chloroform was evaporated under a 40° C. nitrogen stream. The total mass of PHB was determined by weighing (after subtracting a control non-PHB containing mock reaction) and is expressed in terms of g/L. Alternatively, the method of Arikawa et al (2017) was employed. In this method the final bacterial pellet was sonicated in the presence of 0.5% SDS (typical volume was 20 mL from a liter of culture). The insoluble PHB was collected by centrifugation at 15,000× g for 30 minutes, washed in water, recentrifuged, washed in ethanol, recentrifuged, and the final pellet was air dried as above and weighed.

Depolymerization/Polymerization

Method A

Purified PHB depolymerase was added to the supplemented M9 media (minus HB) at a final concentration of 10 mg/mL along with various amounts of PHB film. The flask was maintained at 30° C. with shaking at 250 rpm. Timed aliquots were removed and subjected to the HB assay described. Shaking was continued until all the PHB film was depolymerized (via visual inspection) or the concentration of measured HB plateaued. The flask was boiled for ten minutes to completely inactivate the enzyme, followed by cooling to 30° C. This flask was then inoculated with a fresh culture of washed *L. enzymogenes* to a final concentration of $1.0 \times 10^7$ cfu/mL. Growth was initiated at 30° C. with shaking at 250 rpm and cell numbers were monitored by taking timed aliquots from the flask and measuring optical density at 600 nm. After the onset of stationary phase, the cells were pelleted and PHB was extracted. During the PHB formation phase (in approximately 48-72 hours), the extracellular concentration of HB was measured by removing timed aliquots from the flask and assaying for the concentration of HB as described.

As illustrated in FIG. 2, the purified *L. enzymogenes* PHBDase was efficient at degrading PHB films. Within three hours, all PHB film was converted into HB as is shown in FIG. 2. This HB in turn was efficiently utilized to support the growth of *L. enzymogenes* when it was used as the sole carbon source as shown in FIG. 3 in which the open circles indicate the reduction of HB in the flask and the closed circles indicate bacterial growth. As indicated, over the course of the 72 hour growth experiment, the number of bacteria cells increased (as measured by optical density at 600 nm) and the flask concentration of HB decreased. This method clearly showed that exogenously added HB could be utilized as the sole carbon source by *L. enzymogenes*. Bacterial growth only plateaud when the concentration of HB was undetectable in the assay.

Method B

Purified PHB depolymerase was added to the supplemented M9 media (minus HB) at a final concentration of 10 mg/mL plus various amounts of PHB film. Washed *L. enzymogenes* cells were immediately added to a final concentration of $1.0 \times 10^7$ cfu/mL. The flask was allowed to continue to grow for an additional 72 hours. The cells were pelleted by centrifugation at 15,000× g for 15 minutes and PHB was extracted from the pellet. During the PHB formation phase, the extracellular concentration of HB was measured by removing timed aliquots from the flask and assaying for the concentration of HB as described above.

As indicated in FIG. 4, upon culturing the *L. enzymogenes* in the presence of the PHB and the PHBDase, growth (closed circles) began after a short lag, a period in which some of the PHB film was converted to HB via the purified *L. enzymogenes* PHBDase enzyme. As growth continued, the enzyme hydrolyzed more of the PHB film, releasing HB into the medium (open circles). This can be seen as an early increase in fluorescence emission signal in FIG. 4. As indicated, HB accumulation peaked at approximately six hours at which time there was an increase in bacterial growth (measured as optical density at 600 nm). Growth was linear until approximately hour nine at which time the rate of growth slowed to a lower level of linearity for the rest of the examination period. This demonstrated that purified enzyme was stable in the presence of a growing bacterial culture over the course of the growth period and produced metabolically active HB.

Method C

The supplemented M9 media (minus the HB) was inoculated with washed *L. enzymogenes* cells to a final concentration of $1.0 \times 10^7$ cfu/mL. Various amounts of PHB film were added to the flask. Flasks were maintained at 30° C. with shaking at 250 rpm and cell numbers were monitored by taking timed aliquots from the flask and measuring optical density at 600 nm. These same aliquots were subjected to the HB assay described. The flask was allowed to continue to grow for an 48-72 hours. The cells were pelleted by centrifugation at 15,000× g for 15 minutes and PHB was extracted from the pellet.

As indicated in FIG. 5, the HB did not need to be added exogenously to a growing bacterial culture, nor did a purified enzyme need to be added to the bacterial culture in order to convert a PHB containing product to HB and to further convert that HB into metabolic material that drives the formation of new PHB accumulation in the bacterial cell. As indicated, the *L. enzymogenes* could be used in a single vessel reaction to biochemically drive the overall depolymerization/polymerization reactions. When PHB film and the bacteria were cultured together there was an approximately six hour lag before HB could be detected in the culture (open circles). Bacterial growth (closed circles) beyond the inoculum was not detectable for approximately 12 hours, until there was a degree of HB accumulation in the medium. At that point linear growth began and continued over the course of the examination period until approximately hour 60. The concentration of HB reached a maximum at approximately 34 hours post-inoculation and decreased until hour 60 where it plateaued at a low (but steady) level.

This approach was also examined utilizing a second bacteria species (method C2), *Pseudomonas fluorescens*, as the depolymerization bacteria species. In this case, both genera of bacteria were added at a final concentration of $5.0 \times 10^6$ cfu/mL at time zero. Timed aliquots from the flask were removed to measure total bacterial density (OD at 600 nm) and for assaying for the concentration of HB as described above. The cells were pelleted by centrifugation at 15,000× g for 15 minutes and PHB was extracted from the pellet.

Figure 6:
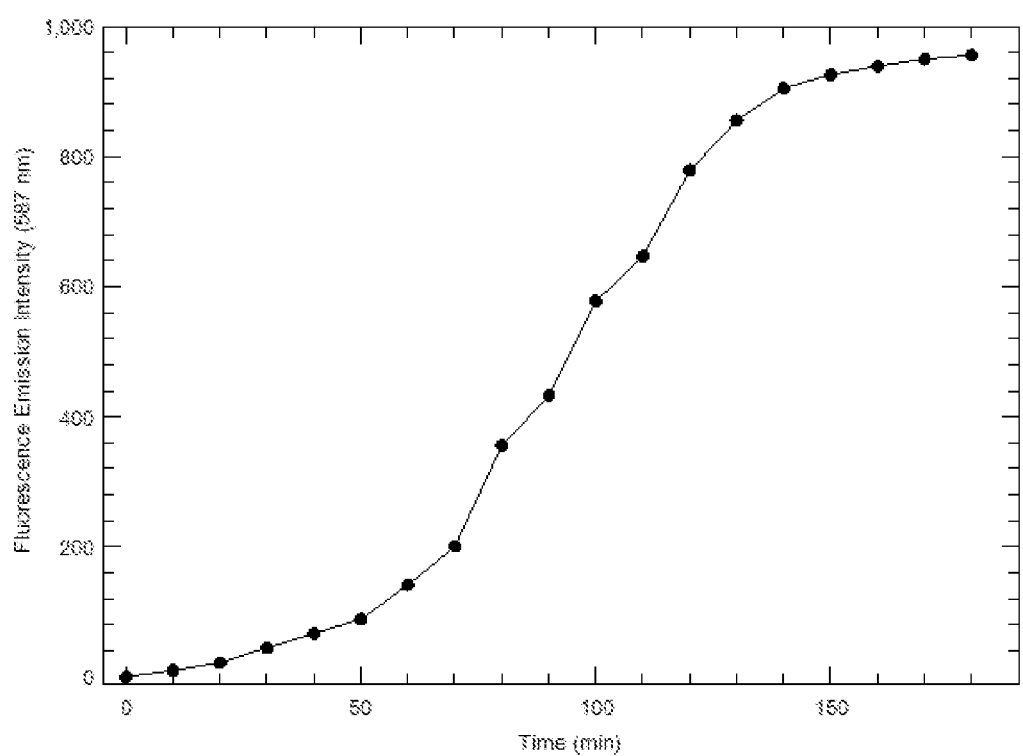
FIG. 6 graphically illustrates the formation of HB monomer upon depolymerization of a PHB polymer using a purified enzyme as described further herein.

*P. fluorescens* secretes a particularly kinetically fast PHBDase. Utilization of such a species could accelerate the rate of a process. As indicated in FIG. 6, Measurable HB (closed circles) was seen in the co-culture within the first hour and reached a plateau maximum between two and 10 hours at which point the HB concentration linearly decreased until hour 50 when it then slowly became unmeasurable. There was a significantly shorter lag period for the onset of *L. enzymogenes* growth (two hours; closed cirecles) compared to the data in FIG. 5. This was solely attributed to the quicker availability of significant levels of HB. *L. enzymogenes* growth was biphasic, the first more rapid growth period between hours two and eight, followed by a slower rate of growth for the rest of the experimental period.

Method D

Mid-log phase *E. coli* Origami-2 expression cells harboring an expression plasmid encoding the *Pseudomonas geniculata* PHBDase (with an added gram negative signal sequence) were added to a final concentration of $1.0 \times 10^7$ cfu/mL in the M9 media (minus the HB) supplemented with 0.5 mM IPTG. The flask also contained various amounts of PHB film. That flask was immediately inoculated with $1.0 \times 10^7$ cfu/mL washed *L. enzymogenes* cells. The flask was maintained at 30° C. with shaking at 250 rpm for 48-72 hours. The cells were pelleted by centrifugation at 15,000× g for 15 minutes and PHB was extracted from the pellet. During the PHB formation phase, the extracellular concentration of HB was measured by removing timed aliquots from the flask and assaying for the concentration of HB as described above.

Figure 7:
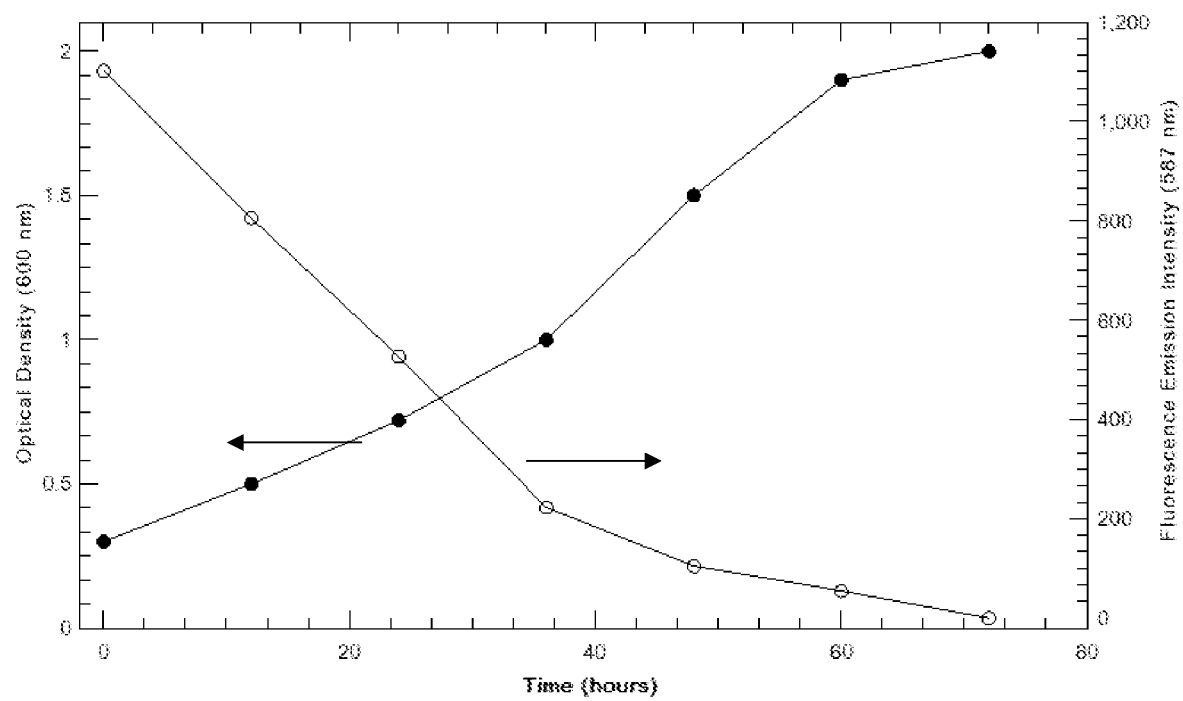
FIG. 7 graphically illustrates the growth of *Lysobacter enzymogenes* bacteria as a function of time (closed circles) and the simultaneous reduction of HB in the flask (open circles) utilizing HB produced by depolymerization of a PHB polymer using a purified enzyme.

In this method, the enzyme was secreted after it is produced in a bacterial expression system in the growth media along with the *L. enzymogenes* culture. The *P. geniculata* PHBDase was cloned into a T7 expression plasmid and the construct was transformed into a competent *E. coli* expression strain. In the presence of IPTG, the bacteria begin to overproduce the enzyme and to secrete it into the medium. This began the depolymerization of the PHB film in the flask and the subsequent growth of the *L. enzymogenes* culture. The expression systems were highly efficient, so the lag period observed was less than 30 minutes before HB was measurable in the fluorescent assay. These results are shown in FIG. 7. Selection pressure was maintained on the *E. coli* by adding ampicillin to the media (the vector contained the amp resistance gene).

At completion of each method, the bacterial cells were collected by centrifugation and frozen at −20° C. until all the experiments were completed. PHB was extracted from the cell mass as described in Methods. A control extraction was processed which contained a similar mass of *L. enzymogenes* bacteria which had been grown in rich media (and therefore should be devoid of intracellular PHB). At the end of the reaction, the total amount of material left in the reaction tubes was weighed and the control extraction mass subtracted from the value. Typically, the mass in the control extraction was only 0.02 g.

Figure 8:
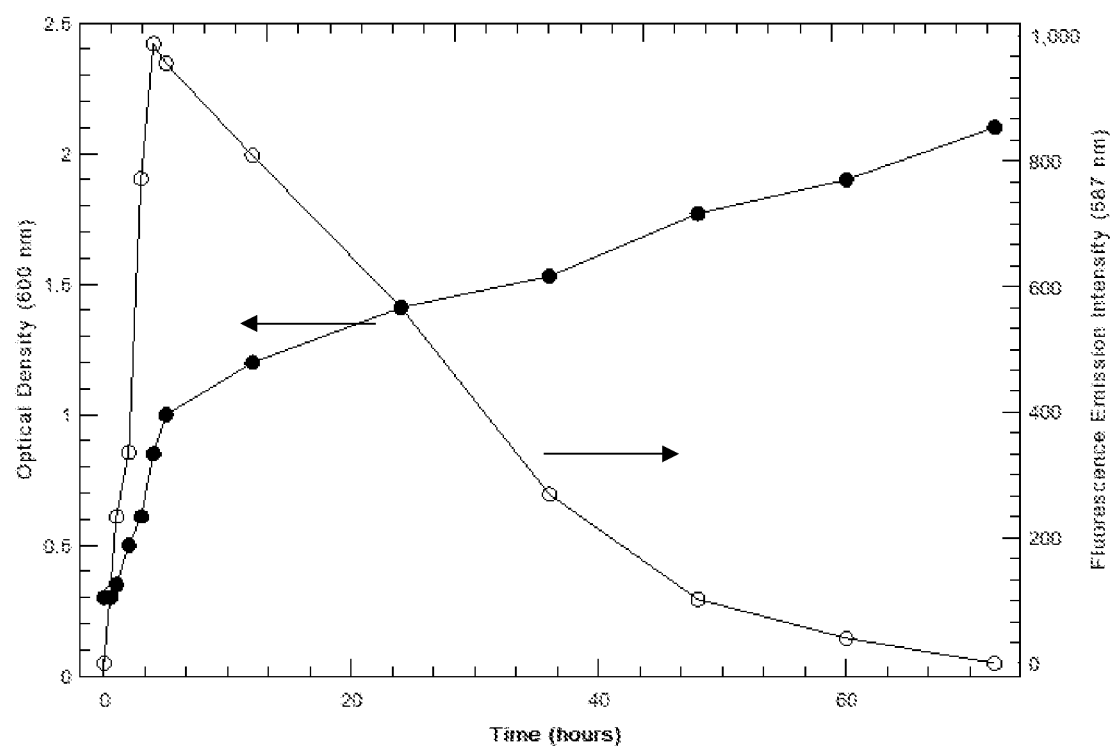
FIG. 8 graphically illustrates the growth of *L. enzymogenes* bacteria as a function of time (closed circles) and the simultaneous concentration of HB in the flask (open circles) under simultaneous depolymerization and polymerization conditions utilizing an added PHBDase in conjunction with the presence of *L. enzymogenes* bacteria.

Resulting extraction data are shown in FIG. 8. As shown, the PHB yields were similar for all of the methods in this work. The control (Con) experiment represented a similar mass of *L. enzymogenes* grown in Tryptic Soy Broth media with glucose as the carbon source. Note should be taken that no effort was made to optimize any of the methods beyond what was described and with such optimization as would be evident to one of skill in the art, increased PHB yields could be attained.

Figure 9:
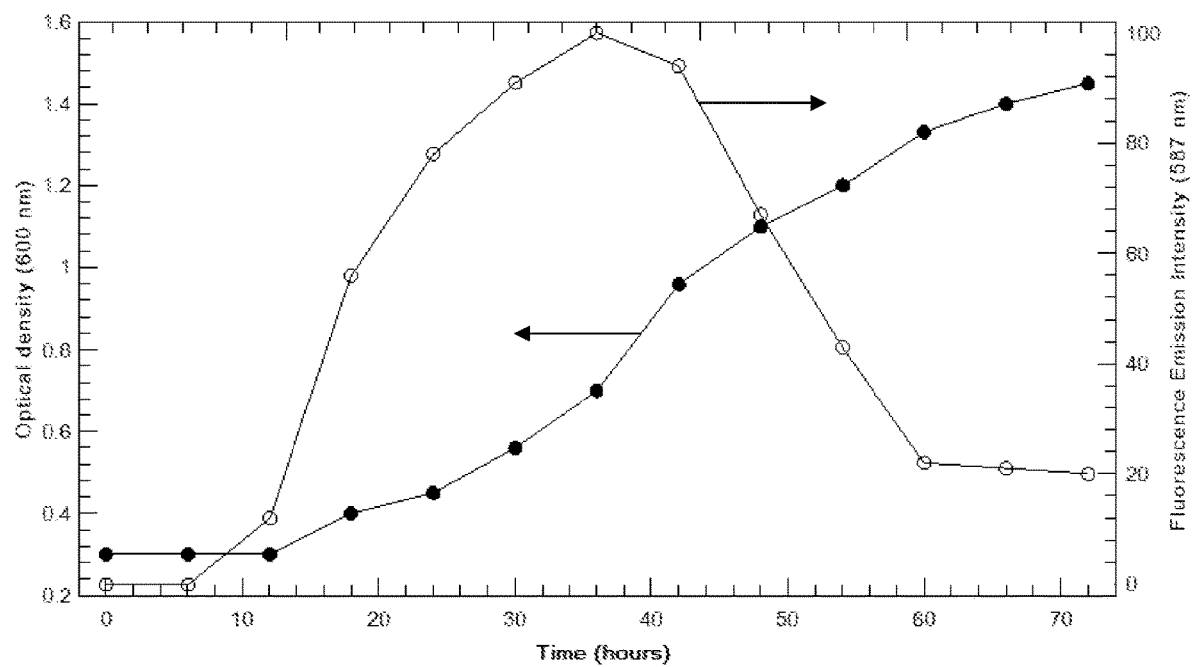
FIG. 9 graphically illustrates growth of *L. enzymogenes* bacteria as a function of time (closed circles) and the simultaneous concentration of HB in the flask (open circles) during depolymerization and polymerization upon utilization of the bacteria to produce the depolymerase.
Figure 10:
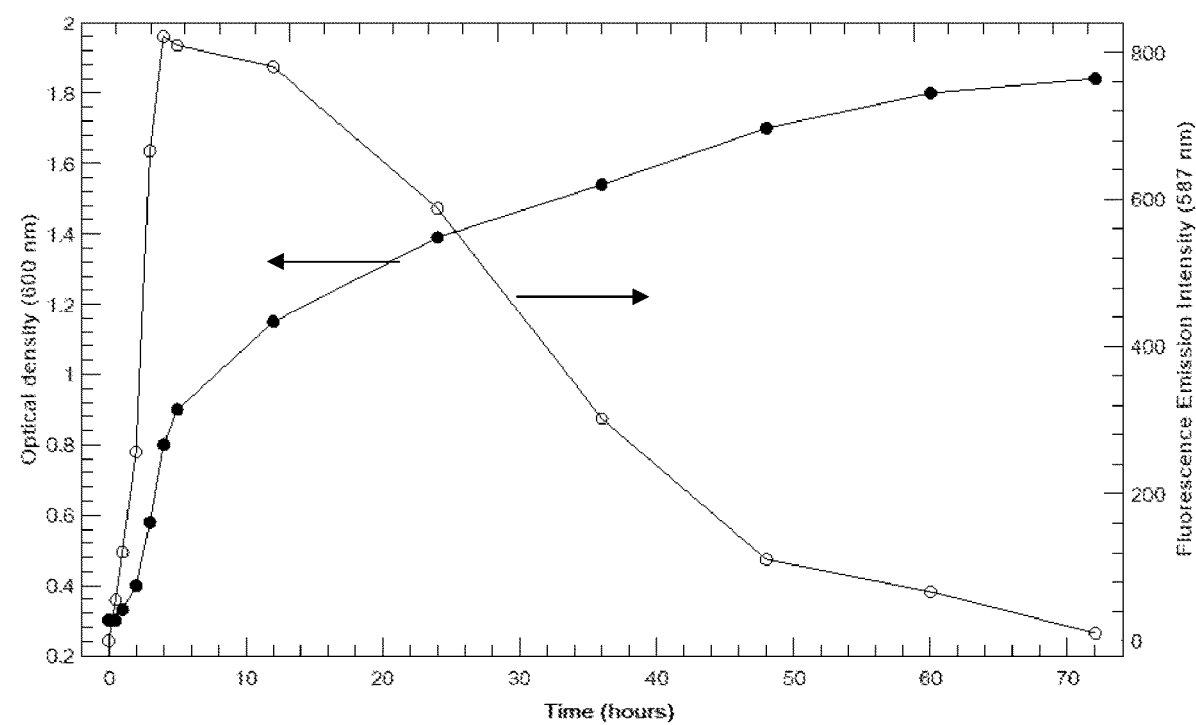
FIG. 10 graphically illustrates growth of a mixed culture of *P. fluorescens* and *L. enzymogenes* bacteria as a function of time (closed circles) and the simultaneous concentration of HB in the flask (open circles) during depolymerization and polymerization upon utilization of the bacteria to produce the depolymerase.
Figure 11:
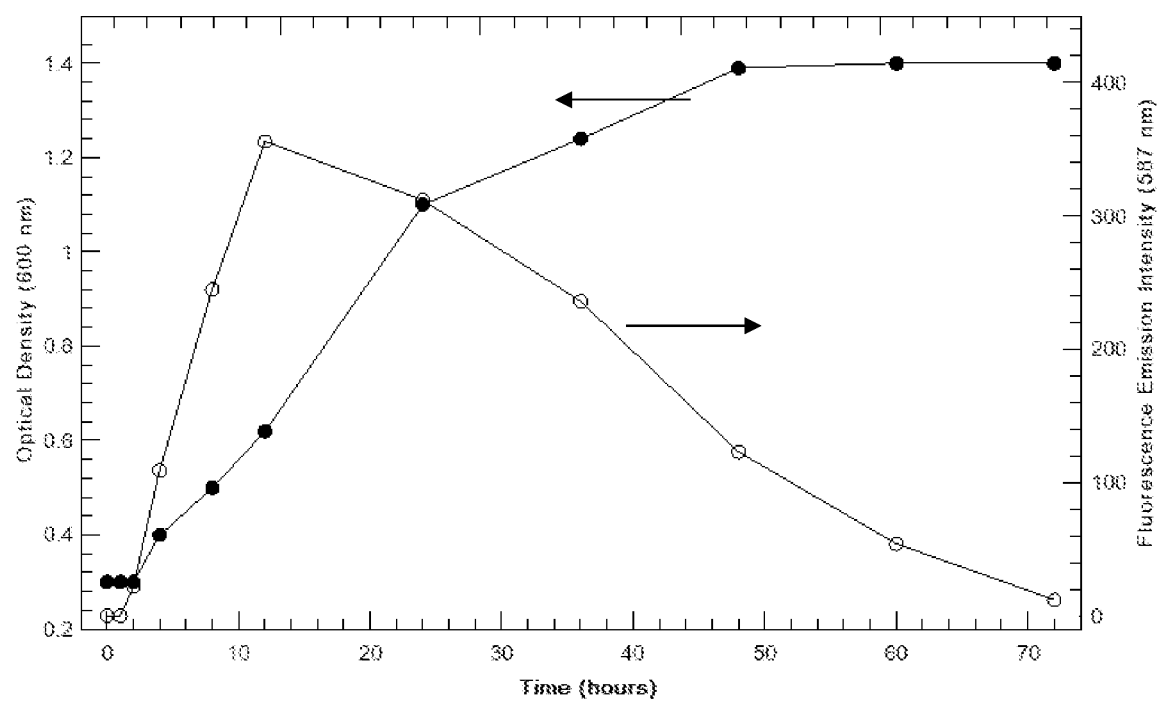
FIG. 11 graphically illustrates growth of a mixed culture including *E. coli* expressing *P. geniculata* PHBDase and *L. enzymogenes* bacteria as a function of time (closed circles) and the simultaneous concentration of HB in the flask (open circles).
Figure 12:
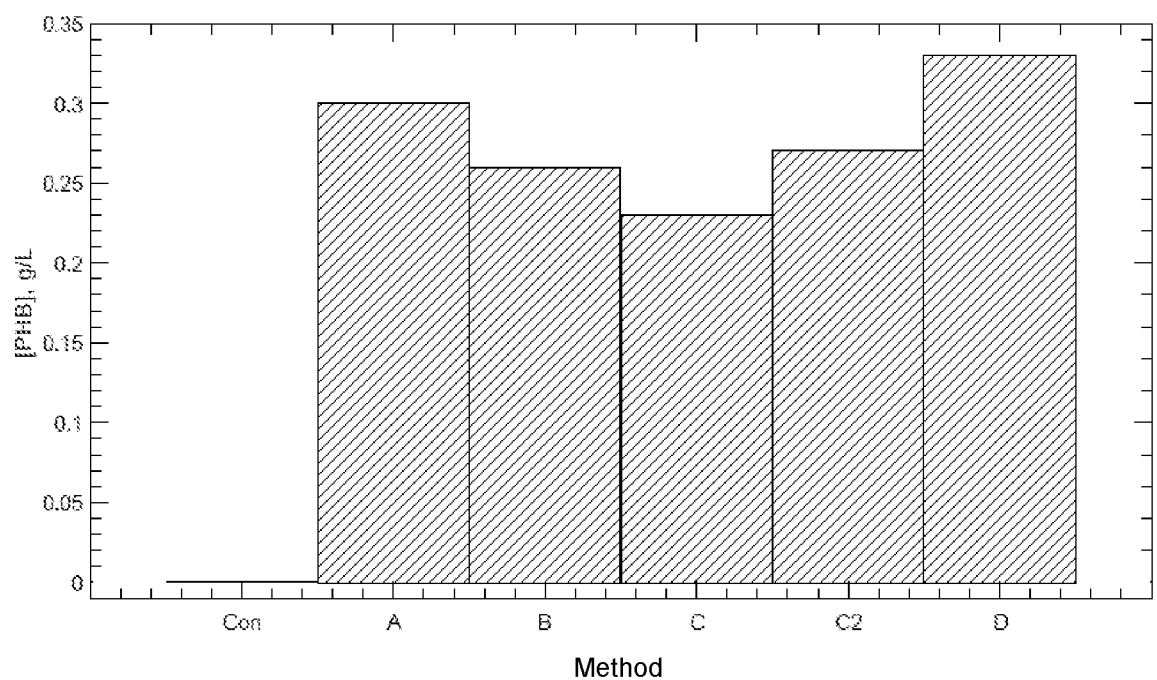
FIG. 12 graphically illustrates the mass of extracted PHB from *L. enzymogenes* in each of the five different methods carried out and described in the example section herein.
Figure 13:
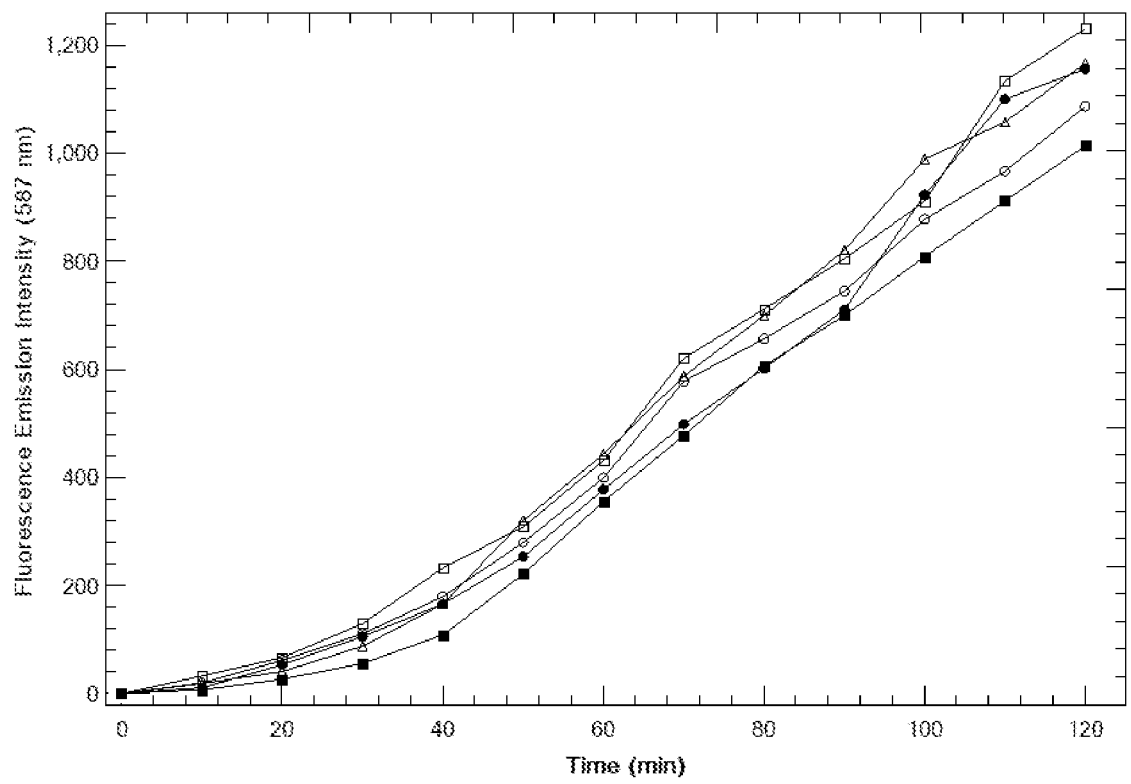
FIG. 13 graphically overlays formation of HB via depolymerization of PHB formed in each of the five different methods carried out and described in the example section herein.

The nature of the extracted material was shown to be PHB by the observation that it could be fully converted to measurable HB using the standard assay. This is shown in FIG. 9 in which the HP formation curve from each of the methods is shown (Method A, closed circles; Method B, open circles; Method C, closed squares; Method C2, open squares; Method D, open triangles). For an equal mass input and the same amount of added enzyme, the kinetics of the depolymerization were nearly identical across all of the examined methods. This illustrates that any of the methods, was well as combination of methods, could be successfully utilized for a circular recycling process.

Example 2

A variety of different bacteria were purchased from the American Type Culture Collection and were propagated and grown in supplemented M9 bacteria as described in Example 1. A depolymerization/polymerization as described according to Method C, above, was carried out utilizing each bacteria. At the end of the growth period, the cells were harvested and internal PHB was isolated and measured as described above. Table 4, below shows the amount of new PHB synthesized by each of the bacteria examined.

TABLE 4

| Organism | ATCC reference | PHB concentration (g/L) |
| --- | --- | --- |
| Acidovorax facilis | 55745 | 0.24 |
| Bacillus thuringiensis | 39756 | 0.52 |
| Dyella japonica | BAA-939 | 0.50 |
| Escherichia coli | BAA-769 | 0.00 |
| Halomonas aquamarina | 35134 | 0.55 |
| Lysobacter antibioticus | 29480 | 0.41 |
| Lysobacter enzymogenes | 29487 | 0.65 |
| Lysobacter gummosus | 39472 | 0.32 |
| Pseudomonas aeruginosa | 10145 | 0.35 |
| Pseudomonas fluorescens | 13525 | 0.56 |
| Rhodanobacter denitrificans | BAA-1447 | 0.48 |
| Shewanella frididmarina | 700550 | 0.80 |
| Thermobifida fusca | 27730 | 0.65 |
| Thermus thermophilus | 27634 | 0.40 |
| Xanthomonas vesicatoria | 35937 | 0.35 |

As can be seen, there was significant variation in recovered PHB both as a function of genus as well as by different species within a genus. For instance, the recovery of PHB from *Acidovorax* (the lowest yielding producer) was 3.3-fold lower than the recovered yield from *Shewanella* (the highest yielding producer). Moreover, within a single genus there were species differences. For instance, in the genus *Lysobacter*, there was a 2-fold difference in recovered PHB between the best species and the worst species. The species level differences were also seen in the genus *Pseudomonas*. Variations can also be expected to occur depending upon growth conditions. Thus, a balance can be struck between identifying a genus that is compatible with the requirements of a process (e.g.—high or elevated temperature, pressure, salt concentration, etc.) and then identifying a species within that genus that maximizes yield or can be optimized to maximize yield.

These and other modifications and variations to the present invention may be practiced by those of ordinary skill in the art, without departing from the spirit and scope of the present invention, which is more particularly set forth in the appended claims. In addition, it should be understood that facets of the various aspects may be interchanged both in whole or in part. Furthermore, those of ordinary skill in the art will appreciate that the foregoing description is by way of example only, and is not intended to limit the invention so further described in such appended claims.

What is claimed:

1. A method for treatment of a post-consumer product, comprising:
   contacting a post-consumer product with a polyhydroxyalkanoate depolymerase (PHADase), the post-consumer product comprising a first polyhydroxyalkanoate, the PHADase catalyzing depolymerization of the first polyhydroxyalkanoate and releasing a hydroxyalkanoate monomer from the first polyhydroxyalkanoate;
   culturing a first microorganism in the presence of the hydroxyalkanoate monomer, the first microorganism being capable of metabolizing the hydroxyalkanoate monomer as a metabolic carbon source, the first microorganism being capable of producing a second polyhydroxyalkanoate, wherein the culturing is carried out under a condition that encourages production of the second polyhydroxyalkanoate by the first microorganism, wherein the first microorganism is selected from the genus *Lysobacter*.

2. The method of claim 1, wherein the first polyhydroxyalkanoate is a first polyhydroxybutyrate.

3. The method of claim 1, wherein the PHADase is a purified enzyme.

4. The method of claim 3, wherein the PHADase is expressed by the first microorganism or is a modified enzyme that includes one or more amino acid modifications as compared to a PHADase expressed by the first microorganism, or wherein the PHADase is expressed by a second microorganism.

5. The method of any of claim 1, wherein the PHADase is expressed by a second microorganism, the method including culturing the second microorganism in the presence of the post-consumer product and thereby contacting the post-consumer product with the PHADase.

6. The method of claim 5, wherein the first microorganism and the second microorganism are the same.

7. The method of claim 5, wherein the second microorganism is a genetically modified microorganism.

8. The method of claim 1, wherein the first microorganism is contacted with the hydroxyalkanoate monomer following completion of the depolymerization of the first polyhydroxyalkanoate.

9. The method of claim 1, wherein the first microorganism is contacted with the hydroxyalkanoate monomer in conjunction with the depolymerization of the first polyhydroxyalkanoate.

10. The method of claim 1, wherein at least one of the contacting step and the culturing step takes place at an extreme condition, wherein the polyhydroxyalkanoate depolymerase comprises an extremozyme.

11. The method of claim 10, the extreme condition comprising one or more of a salt concentration of about 0.5 M or greater, a temperature of about 40° C. or greater or a temperature of about 10° C. or less, a pressure of about 0.5 MPa or greater, a pH of from about 1 to about 5.5 or a pH of about 7.5 to about 11.5, in the presence of ionizing radiation of about 1000 Gy or greater, or any combination thereof.

12. The method of claim 1, wherein the condition that encourages production of the second polyhydroxyalkanoate by the first microorganism comprises one or more of the following:
   metabolic carbon source other than the hydroxyalkanoate monomer present at a concentration of about 2 millimolar or less;

deprivation of nitrogen-containing nutrients;
deprivation of phosphate-containing nutrients;
an environmental condition at or near a limit of the environmental condition at which the microorganism survives.

13. The method of claim 1, wherein the condition that encourages production of the second polyhydroxyalkanoate by the first microorganism comprises providing the hydroxyalkanoate monomer as the only metabolic carbon source in the culture.

14. The method of claim 1, wherein the condition that encourages production of the second polyhydroxyalkanoate by the first microorganism comprises metabolic carbon source other than the hydroxyalkanoate monomer present at a concentration of about 2 millimolar or less.

15. The method of claim 1, wherein the first microorganism is selected from *Lysobacter aestuarii, Lysobacter antibioticus, Lysobacter bugurensis, Lysobacter capsica, Lysobacter lacus, Lysobacter lycopersici, Lysobacter maris, Lysobacter niastensis, Lysobacter profundi, Lysobacter* sp. A03, *Lysobacter* sp. cf310, *Lysobacter* sp. H21R20, *Lysobacter* sp. H21R4, *Lysobacter* sp. H23M41, *Lysobacter* sp. R19, *Lysobacter* sp. Root604, *Lysobacter* sp. Root690, *Lysobacter* sp. Root916, *Lysobacter* sp. Root983, *Lysobacter* sp. TY2-98, *Lysobacter spongiae, Lysobacter spongiicola, Lysobacter alkalisoli, Lysobacter arseniciresistens, Lysobacter daejeonensis, Lysobacter dokdonensis, Lysobacter gilvus, Lysobacter gummosus, Lysobacter maris, Lysobacter oculi, Lysobacter panacisoli, Lysobacter penaei, Lysobacter prati, Lysobacter psychrotolerans, Lysobacter pythonis, Lysobacter ruishenii, Lysobacter segetis, Lysobacter silvestris, Lysobacter silvisoli, Lysobacter soli, Lysobacter* sp. 17J7-1, *Lysobacter* sp. Alg18-2.2, *Lysobacter* sp. Cm-3-T8, *Lysobacter* sp. H23M47, *Lysobacter* sp. HDW10, *Lysobacter* sp. II4, *Lysobacter* sp. N42, *Lysobacter* sp. OAE881, *Lysobacter* sp. Root494, *Lysobacter* sp. URHA0019, *Lysobacter* sp. WF-2, *Lysobacter* sp. yr284, *Lysobacter tabacisoli, Lysobacter telluris, Lysobacter tolerans, Lysobacter xinjiangensis.*

16. A system for carrying out the method of claim 1, wherein the system includes a single vessel within which the step of contacting and the step of culturing both take place or wherein the system includes a first vessel within which the step of contacting takes place and includes a second vessel within which the step of culturing takes place.

17. The method of claim 4, wherein the second microorganism is a genetically modified microorganism.

18. The method of claim 1, wherein the first microorganism comprises a *Lysobacter enzymogene*.

* * * * *